United States Patent
Bilbao et al.

(12)

(10) Patent No.: US 6,436,393 B1
(45) Date of Patent: Aug. 20, 2002

(54) ADENOVIRAL VECTOR ENCODING ANTI-APOPTOTIC BCL-2 GENE AND USES THEREOF

(76) Inventors: Guadalupe Bilbao, 130 Stratford Cir.; David T. Curiel, 824 Linwood Dr.; Juan L. Contreras, 130 Stratford Cir., all of Birmingham, AL (US) 35222

( * ) Notice: Subject to any disclaimer, the term of this patent is extended or adjusted under 35 U.S.C. 154(b) by 0 days.

(21) Appl. No.: 09/301,836

(22) Filed: Apr. 29, 1999

Related U.S. Application Data

(60) Provisional application No. 60/083,434, filed on Apr. 29, 1998.

(51) Int. Cl.[7] ................ A01N 63/00; A01N 43/04; C12N 15/00; C12N 5/00; C12N 15/63
(52) U.S. Cl. ............... 424/93.2; 424/93.21; 424/93.6; 435/320.1; 435/325; 435/455; 514/44
(58) Field of Search .................. 424/93.21, 93.6, 424/93.2; 435/320.1, 325, 69.1, 455; 514/44; 536/23.5

(56) References Cited

U.S. PATENT DOCUMENTS

| | | | |
|---|---|---|---|
| 5,585,362 A | 12/1996 | Wilson et al. | |
| 5,834,306 A | 11/1998 | Webster et al. | 435/320.1 |
| 6,027,721 A | 2/2000 | Hammang et al. | 424/93.2 |

OTHER PUBLICATIONS

Miller et al., "Targeted vectors for gene therapy." FASEB Journal, vol. 9: 190–199, Feb. 1995.
Deonarain M., "Ligand–targeted receptor–mediated vectors for gene delivery." Exp. Opin. Ther. Patents, vol. 8(1): 53–69, 1998.
Crystal R., "Transfer of Genes to Humans: Early Lessons and Obstacles to Success." Science, vol. 270: 404–410, Oct. 1995.
Verma et al., "Gene therapy– promises, problems, and prospects." Nature, vol. 389: 239–242, Sep. 1997.
O'Reilly Lorraine A. et al., "The cell death inhibitor Bcl–2 and its homologues influence control of cell cycle entry." EMBO Journal 15 (24):p 6979–6990, 1996.
Dole Mukund G. et al., "Bcl–x/s enhances adenoviral vector–induced apoptosis in neuroblastoma cells." Cancer Research 56 (24): p5734–5740, 1996.
Yamabe Kazuo et al., "Prevention of hypoxic liver cell necrosis by in vivo human bcl–2 gene transfection." Transplantation Proceedings, vol. 29, No. 1–2, p384–385, 1997.
Yamabe Kazuo et al., "Prevention of hypoxic liver cell necrosis by in vivo human bcl–2 gene transfection." Biochemical and Biophysical Research Communications, vol. 243, No. 1,p217–223, Feb. 1998.
Vanhaesebroeck Bert et al., "Effect of bcl–2 proto–oncogene expression on cellular sensitivity to tumor necrosis factor-mediated cytotoxicity." Oncogene, vol. 8 (4), p1075–1081, 1993.*
Marcellus et al. Adenovirus Type 5 Early Region 4 is Responsible for E1A–Induced P53–Independent Apotosis *Journal of Virology*, (1996), 70:6207–6215.

* cited by examiner

*Primary Examiner*—Scott D. Priebe
*Assistant Examiner*—Sumesh Kaushal
(74) *Attorney, Agent, or Firm*—Benjamin Aaron Adler

(57) ABSTRACT

The present invention provides an adenoviral vector encoding an anti-apoptotic Bcl-2 gene for cytoprotection, gene therapy, and cellular and organ transplantation. Also provided are various methods of using said adenoviral vector to protect cells for cellular transplantation, or organs for both allotransplantation and xenotransplantation, to improve organ preservation for transplantation, to reduce ischemial/reperfusion injury, to protect endothelial cells from various inducers of injury, and to prolong transgene expression.

6 Claims, 28 Drawing Sheets

(2 of 28 Drawing Sheet(s) Filed in Color)

FGD

```
SEQUENCE LISTING

<160> NUMBER OF SEQ ID NOS: 2

<210> SEQ ID NO 1
<211> LENGTH: 20
<212> TYPE: DNA
<213> ORGANISM: artificial sequence
<220> FEATURE:
<221> NAME/KEY: primer_bind
<223> OTHER INFORMATION: primer for PCR amplification to generate human
      Bcl-2-specific fragment ([]590 bp)

<400> SEQUENCE: 1
agtgggatgc gggagatgtg                                              20

<210> SEQ ID NO 2
<211> LENGTH: 20
<212> TYPE: DNA
<213> ORGANISM: artificial sequence
<220> FEATURE:
<221> NAME/KEY: primer_bind
<223> OTHER INFORMATION: primer for PCR amplification to generate human
      Bcl-2-specific fragment ([]590 bp)

<400> SEQUENCE: 2
ggggccgtac agttccacaa                                              20
```

ADENOVIRAL VECTOR ENCODING ANTI-APOPTOTIC BCL-2 GENE AND USES THEREOF

CROSS REFERENCE TO RELATED APPLICATION

This patent application claims benefit of provisional patent application U.S. Ser. No. 60/083,434, filed Apr. 29, 1998, now abandoned.

FEDERAL FUNDING LEGEND

This invention was created in part using federal funds under grant NIH CA 72532-01. Consequently, the United States government has certain rights in this invention.

BACKGROUND OF THE INVENTION

1. Field of the Invention

The present invention relates generally to the fields of gene therapy and transplantation. More specifically, the present invention relates to an adenoviral vector encoding an anti-apoptotic Bcl-2 gene for cytoprotection, gene therapy, and cellular and organ transplantation.

2. Description of the Related Art

The delineation of the molecular basis of cancer allows for the possibility of specific intervention at the molecular level for therapeutic purposes. To an increasing extent, the genetic lesions associated with malignant transformation and progression are being identified [1–3]. Thus, not only in the context of inherited genetic diseases, but also for many acquired disorders, characteristic errors in patterns of gene expression may be precisely defined. Based on this understanding, the rationale to develop novel therapeutic modalities on gene therapy approaches has become increasingly compelling.

The elucidation of the genetic basis of inherited and acquired diseases have rendered gene therapy both a novel and rational approach for these disorders [4–14]. To this end, three main strategies have been developed: mutation compensation, molecular chemotherapy, and genetic immunopotentiation. For mutation compensation, gene therapy techniques are designed to rectify the molecular lesions in the cancer cell etiologic of malignant transformation. For molecular chemotherapy, methods have been developed to achieve selective delivery or expression of a toxin gene in cancer cells to achieve their eradication. Genetic immunopotentiation strategies attempt to achieve active immunization against tumor-associated antigens by gene transfer methodologies. For these conceptual approaches, human clinical protocols have entered Phase I clinical trials to assess dose escalation, safety, and toxicity issues.

Two general approaches have been employed. Firstly, the ex vivo approach, whereby target cells are genetically modified extracorporally, followed by reimplantation. This strategy capitalizes on the fact that the current generation of vectors can achieve efficient gene transfer in vitro, as well as in the fact that a level of biosafety characterization is achievable. Despite the fact that this strategy has been employed successfully in a number of animal model systems to achieve genetic correction, the translation into human clinical trials has yielded only a relatively few parenchymal cells that were manipulated. Whereas these methods have been of utility for selected disease contexts, for many disease states this approach does not offer a practical means to achieve a meaningful genetic intervention. Based on this concept, a second approach for gene therapy has been developed based on direct, in vivo delivery of therapeutic genes to target parenchymal cells in situ within their organ context.

For direct in vivo gene transfer, a variety of vector systems have been evaluated in a loco-regional context. These include viral vectors, such as adenovirus, retrovirus, herpes virus vectors, and adeno-associated virus (AAV). In addition, nonviral vectors have been employed to this end, including liposomes, molecular conjugates, polymers and other vectors. In general, despite their utilities, these vectors have been limited in their ability to accomplish highly efficient in vivo gene delivery to relevant target organs. In this regard, the development of strategies to target airway epithelium for cystic fibrosis (CF) gene therapy has allowed the analysis of the gene transfer dynamics of a variety of vector approaches in this context [15–20]. In these studies, a low level of in vitro gene transfer was noted with both types of vectors. However, recombinant adenoviral vectors achieved the highest levels of in situ gene transfer to airway epithelium [21–25].

Based on these results, human clinical trials were developed employing adenoviral vectors [26]. Further, for metabolic and blood disorders, such as hemophilia, in vivo gene therapy approaches have been developed largely via in vivo gene transfer to the liver [27–28]. Here again, the highest levels of transduction of hepatocyte parenchymal cells after in vivo gene delivery have been observed with adenoviral vectors [29–31]. Thus, adenoviral vectors have shown the highest efficiency of in vivo gene delivery in the context of in situ transduction to a variety of parenchymal cells [32].

There are additional advantages to using adenoviral vectors. First, the adenovirus has been extensively studied and is the most widely employed gene therapy vector. Secondly, adenovirus has been produced consistently with high titers. Thirdly, with the use of new recombinant technologies the risk for replication-competent adenovirus in the preparations is low [33]. Fourthly, previous limitations concerning the size of therapeutic gene inserts into the adenovirus genome have been superceded with the development of recombinant adenovirus deleted in multiple early and late genes. Fifthly, recent evidence has shown that inducible systems can be developed in the adenovirus context such as the tetracycline on/off and Cre/Loxp systems [34–35]. Finally, the delivery and/or expression of adenoviral-encoded transgenes can be targeted to the appropriate set of cells by a variety of mechanisms, including modifications of the binding properties of the adenovirus as well as regulation of expression of transgenes by tissue or tumor specific promoters [36].

Loss of adenoviral transfected cells rather than transgene extinction has been suggested as an important factor responsible for limited in vivo expression of therapeutic genes. Cytoprotection of the viral-vector host cells against the immune system and the cytotoxic effects of the viral products may allow significant prolongation of the transgene expression. Cells and organs which express Bcl-2 are more resistant to cytotoxic effects of T lymphocytes, cytokines, free oxygen radicals and other mediators of the immune system.

Programmed cell death or apoptosis plays an important role in a wide variety of physiological processes, including for example removal of redundant cells during development, elimination of autoreactive lymphocytes, and eradication of older, differentiated cells in most adult tissues with self-renewal capacity. Disregulation of this physiological mechanism for cell death has been implicated in a variety of human diseases, ranging from cancer to autoimmunity, where insufficient cell death can figure prominently, to AIDS and neurodegenerative disorders, where excessive death of T-lymphocytes and neurons occurs as well as in acute diseases such as infection, ischemia-reperfusion damage and infarction. The process of cell death and its morphological equivalent "apoptosis" can be subdivided into three different phases: initiation, effector and degradation. Whereas the initiation stage depends on the type of apoptosis-inducing stimulus (grow factor deprivation, cytokines, thermal/mechanical injury, irradiation, etc.) the effector (which is still subject to regulation) and degradation (beyond regulation) stages are common to all apoptotic processes.

The family of bcl-2 related proteins constitutes one of the most biologically relevant classes of apoptosis-regulatory gene products acting at the effector stage of apoptosis. Several biological effects of bcl-2 on intact cells have been reported. Bcl-2 might act on plasma membrane (prevention of phosphatidylserine), on the cellular redox potential (decrease lipid peroxidation, inhibition of reactive oxygen species, increase in catalase and superoxide dismutase, elevated NAD-/NADH ratio), effects on proteases (inhibition of caspase 3 and 6). Other effects of bcl-2 include effects on intracellular ions (prevention of cytoplasmic acidification, inhibition of $Ca^{++}$ uptake into the nucleus) and effects on mitochondria (inhibition of pre-apoptotic mitochondrial transmembrane potential disruption, prevention of $Ca^{++}$ influx, prevention of cytochrome C outflow from the intermembrane space, etc.). One of the first common manifestations of the apoptotic process, irrespective of the cell type and the induction stimulus, is a disruption of the mitochondrial membrane function that marks the "point of no return" of the apoptotic process. Given the functional importance of bcl-2 gene in apoptosis control, it constitutes prime targets for therapeutic interventions on numerous disease states.

Islet transplantation is associated with high incidence of primary non-function. Organ damage has been demonstrated since organ procurement, preservation and reperfusion. In the case of the pancreatic islets, additional "insulting" factors like the islet isolation, culture, poor vascularization and proinflammatory cytokine release after transplantation make the islet transplantation a high risk procedure for primary non-function. In normal physiology the islets are vascularized by an afferent arteriole (arterial blood) and are innervated by cholinergic adrenergic and peptidenergic innervations. In a period of weeks after transplantation, the islets are not normally vascularized. In the case of intraportal administration, immediately after transplantation, islets are vascularized by only portal venous blood and after a period of several weeks are presumably vascularized by hepatic arterial blood. The changes in the vascular and neurophysiological environments may be coincident with the complete normal islet function. Poor islet vascularity early after transplantation has been determined as an important cause of islet dysfunction and survival after transplantation. Infiltration of the pancreatic islets by immune/inflammatory cells (insulitis), followed by loss of the insulin producing beta cells is the characteristic histological feature of insulin-dependent diabetes mellitis (IDDM). Islet cell destruction may involve direct contacts between the infiltrating monocytic/lymphocytic cells and islet beta cells and/or may result from the release of soluble mediators from the effector immune cells. Cytokines produced by activated cells infiltrating islets are candidate molecules mediating impaired function and destruction of beta cells in IDDM. Products of inflammation, such as Interleukin-1β and nitric oxide, has been shown to impair early function of pancreatic islets after intrahepatic transplantation. Rabinovitch et al has reported DNA fragmentation as an early event in cytokine induced beta cell destruction.

Liver graft function after transplantation is determined largely by the quality of the donor organ at harvest and the secondary damage during the hypothermic preservation time, warm ischemia and reperfusion injury. These processes may also play a role in the incidence of rejection, vascular and biliary complications, and overall graft and patient survival. Experimental evidence suggested that ischemic injury involves a loss of mitochondrial respiration and consequently ATP depletion. Although cell necrosis is the assumed end-result of preservation and ischemia-reperfusion injury, programmed cell death (apoptosis) results from these identified mechanisms of ischemic injury and has been demonstrated during preservation-induced damage to cultured endothelial cells, liver preservation, and is a frequent event in post-reperfusion biopsy specimens of human liver grafts. Apoptosis has been observed mainly in hepatocytes and sinusoidal lining cells and its intensity correlates with postoperative signs of hepatocyte injury. Genetic modification of liver grafts with the proposed recombinant adenovirus vector might allow the use of "marginal liver grafts", such as livers from old donors, fatty livers, etc.

The significance of ischemia-reperfusion injury in organ transplantation is clearly an important determinant of early and late graft dysfunction. The mechanism and mediators involved in the ischemia/reperfusion injury of liver allografts remain unknown, various etiologic factors have been identified, these include activation of proteases and phospholipases, alteration in calcium concentrations, ATP depletion, cell damage by free radicals, cytokines, chemokines and edothelins, inhibition of nitric oxide synthesis and an active role of cell of the immune system, such as neutrophils and kuppfer cells. Apoptosis is a frequent event in post-reperfusion biopsy specimens of human liver grafts, its main cellular target are hepatocytes and sinusoidal lining cells and its intensity correlates with postoperative signs of hepatocyte injury.

Apoptosis of endothelial cells has been described during organ preservation for transplantation. Cytoprotection of endothelial cells represent an attractive alternative for improved organ preservation. Apoptosis also plays an important role in vascular disease like atherosclerosis, therefore, cytoprotection of endothelial cells might prevent the development of atherosclerotic changes secondary to multiple stimuli, including chronic rejection in clinical transplantation.

The prior art is deficient in the lack of an adenoviral vector encoding a functional anti-apoptotic Bcl-2 gene. Further, the prior art is deficient in the lack of effective means of genetic cytoprotection using an adenoviral vector encoding an anti-apoptotic Bcl-2 gene. The present invention fulfills this long-standing need and desire in the art.

SUMMARY OF THE INVENTION

The present invention is the first description of an adenoviral vector type 5 (E1 deleted) construct capable of producing a functional human Bcl-2 molecule. This approach has applicability to protect adenoviral vector transduced cells, to improve organ preservation for transplantation, to protect from ischemia/reperfusion injury, to protect cells after cellular transplantation, or organs for both allotransplantation and xenotransplantation, and to protect endothelial cells from various inducers of injury.

In one embodiment of the present invention, there is provided an adenoviral vector encoding an anti-apoptotic Bcl-2 gene. Preferably, the adenoviral vector is type 5 with E1 deleted and contains an expression cassette with the Bcl-2 gene under the control of a cytomegalovirus promoter. Preferably, the Bcl-2 gene is human Bcl-2 gene.

In another embodiment of the present invention, there are provided various applications of the disclosed adenovirus vector, including reducing ischemia/reperfusion injury to the liver, improving organ preservation for transplantation, cytoprotecting endothelial cells during cold preservation, cytoprotecting pancreatic islets, and enhancing/prolonging expression of a transgene in a cell.

In still another embodiment of the present invention, there is provided a pharmaceutical composition, comprising the disclosed adenoviral vector and a pharmaceutically acceptable carrier.

Other and further aspects, features, and advantages of the present invention will be apparent from the following description of the presently preferred embodiments of the invention given for the purpose of disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
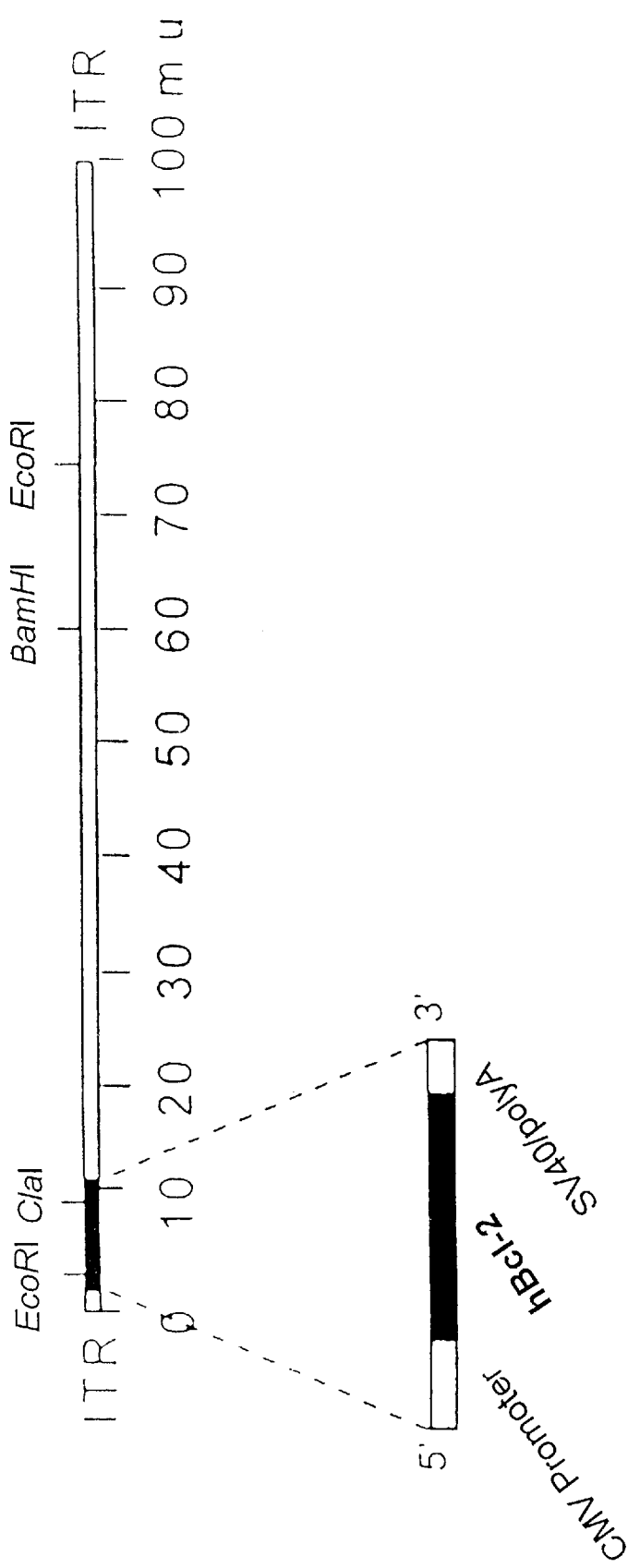
FIG. 1 shows generation of a recombinant adenovirus vector encoding the human Bcl-2 gene (AdCMVhBcl-2). The AdCMVhBcl-2 contains from the left of the adenovirus genome, the cytomegalovirus promoter, the human Bcl-2 open reading frame, followed by SV40poly(A) sequence.

Pancreatic islet transplantation is an attractive alternative for the treatment of diabetes mellitus, has the advantage of a low morbidity transplantation procedure, relatively low cost, and the possibility of islet genetic modification ex vivo and the potential of cell protection, tolerance induction with eventual transplantation without immunosuppression. Pancreatic islet transplantation, however, has been difficult to implement and is not a clinical reality. Islet damage and programmed cell death (apoptosis) occurs during pancreas procurement, preservation, islet isolation, culture and early after transplantation until complete vascularization is achieved.

The family of Bcl-2 related proteins constitutes one of the most biologically relevant classes of apoptosis-regulatory gene products. The cytoprotection of pancreatic islets induced by genetic modification with an adenovirus-mediated gene transfer of the human Bcl-2 gene during long-term islet cultures has been demonstrated in the present invention. The techniques described herein can be also applying to artificial liver support systems.

The vascular endothelial cells of donor organs have been shown to be primarily injured during the cold preservation and reperfusion. The integrity of the vascular endothelium in transplantation plays a critical role for the survival of the graft. Endothelial cells are central to the development of immune inflammatory processes such as graft rejection and endothelial cell death has been associated with vascular disease such as atherosclerosis. Despite the better understanding of the pathogenesis of endothelial cell damage during preservation and the subsequent ischemia-reperfusion injury, effective treatment remains elusive.

In the present invention, genetic modification of endothelial cells to increase their resistance during the preservation time with an adenoviral vector encoding the anti-apoptotic human Bcl-2 gene is disclosed. Genetic modification of endothelial cells can be also applicable to any circumstance when endothelial cells are injured, such as xenotransplantation.

Ischemia/reperfusion injury to the liver is of major importance in numerous clinical situations including hepatic surgery, liver transplantation, shock states, and thermal injury. It has been demonstrated that apoptosis occurs in the period of cold ischemia, anaerobic rewarming, and reperfusion in liver transplantation. Strategies to protect the liver from damage by ischemia/reperfusion are essential. The present invention has also demonstrated gene transfer of the anti-apoptotic Bcl-2 gene with an adenoviral vector into the liver to reduce the ischemia/reperfusion injury.

Early graft function after liver transplantation is determined largely by the quality of the donor organ at retrieval and the secondary influences of hypothermic preservation, flush, and reperfusion injury. These processes may also play a role in the frequency of rejection, the development of vascular and biliary complications, and overall graft survival. Cell death (apoptosis) plays an important role in a wide variety of pathophysiological circumstances including organ preservation. The present invention has demonstrated that genetic modification of the liver graft with a recombinant adenoviral vector encoding the Bcl-2 gene reduces apoptosis during the preservation time.

Recombinant adenoviral vectors have found broad utility for a variety of gene therapy applications. This fact derives principally from their ability to accomplish efficient in vivo gene transfer in a variety of organ contexts. Successful employment of these agents for gene therapy purposes, however, has been significantly limited to date. This is largely to the fact that an invariable consequence of in situ cellular transduction by adenoviral vectors at distinct parenchymal sites is a significant host immunological response against transduced cells. A number of specific immune effector mechanisms, together with nonspecific defense mechanisms, are called into play to eliminate an infecting virus. This process has been associated with attenuation of expression of the transferred therapeutic gene based, at least in part, on loss of the vector transduced cells. The present invention has examined the gene transfer of the anti-apoptotic Bcl-2 gene into the liver to evaluate protection and prolongation of transgene expression.

The present invention is directed to an adenoviral vector encoding an anti-apoptotic Bcl-2 gene. Preferably, the adenoviral vector is type 5 with E1 deleted and contains an expression cassette with the Bcl-2 gene under the control of a cytomegalovirus promoter. Preferably, the Bcl-2 gene is human Bcl-2 gene.

It is specifically contemplated that pharmaceutical compositions may be prepared using the novel adenoviral vector of the present invention. In such a case, the pharmaceutical composition comprises the novel adenoviral vector of the present invention and a pharmaceutically acceptable carrier. A person having ordinary skill in this art would readily be able to determine, without undue experimentation, the appropriate dosages and routes of administration of the novel adenoviral vector of the present invention.

The present invention is also directed to a method of reducing ischemia/reperfusion injury in the liver of an individual in need of such treatment, comprising the step of contacting the liver or liver cells with the disclosed adenoviral vector.

The present invention is also directed to a method of improving organ preservation, comprising the step of contacting the organ with the disclosed adenoviral vector.

Further provided in the present invention is a method of cytoprotecting endothelial cells during cold preservation, comprising the step of transfecting endothelial cells with the novel adenoviral vector disclosed herein. Preferably, this transfection decreases apoptosis rate of the endothelial cells.

The present invention is also directed to a method of cytoprotecting pancreatic islet cells, comprising the step of transfecting the pancreatic islet cells with the adenoviral vector. A lower DNA fragmentation value represents a lower apoptosis rate reflecting cytoprotection of pancreatic islets.

The present invention is further directed to a method of enhancing/prolonging expression of a transgene in a cell, comprising the steps of transfecting the cell with the adenoviral vector and co-expressing the Bcl-2 gene with the transgene in the same cell. Such method enhances the transgene expression by up to 2 log. Preferably, the transgene is a therapeutical gene.

The following examples are given for the purpose of illustrating various embodiments of the invention and are not meant to limit the present invention in any fashion.

EXAMPLE 1
Animals

Normal male and female C57BL/6 mice (Jackson Laboratory, Bar Harbor, Me.) 9 to 12 weeks old weighing 25–30 g, were fed on a laboratory diet with water and food ad libitum and performed surgical procedures at the same hour to avoid circadian variations.

In addition, Landrace-Yorkshire neonatal pigs, 1–3 days old (1.5–2.5 kg/body weight), of either sex, were used as pancreas donors. Male SCID mice (Jackson Laboratory, Bar Harbor, Me.), 9 to 12 weeks old (25–30 g), fed on a laboratory diet with water and food ad libitum, were used as pancreas recipients.

EXAMPLE 2
Cell Lines and Culture Conditions

Human umbilical vein endothelial cells (HUVEC's) were obtained from Dr. F. M. Booyse (Birmingham, Ala., USA). Cells were obtained between the second and third passage. The primary culture of HUVEC's were maintained in 199 media (Mediatech/Cellgro), supplemented with 20% heat-inactivated fetal calf serum (FCS) from HyClone Laboratories (Road Logan, Utah), heparin 80 $\mu$g/ml, endothelial cell growth supplement at 30 $\mu$g/ml (Sigma, Po), L-glutamine at 0.68 mM, penicillin (100 IU/ml), and streptomycin (25 (g/ml). The 293 cell line were obtained from the American Type Culture Collection (Rockville, Md. USA), and were grown in monolayers in Dulbecco's modified Eagle's Medium-Ham's F12 50:50 mixture (DMEM-F12, Mediatech/Cellgro), supplemented with 10% heat-inactivated FCS (HyClone Lab), L-glutamine (200 $\mu$/ml), penicillin (100 IU/ml), and streptomycin (25 $\mu$g/ml). All culture were maintained at 37° C., in a humidified 5% $CO_2$/air atmosphere.e EXAMPLE 3
Generation of Recombinant Adenovirus Vectors Encoding the Human Bcl-2 Gene A recombinant, E1 deleted adenovirus carrying the human Bcl-2 gene under the control of the cytomegalovirus promoter (AdCMVhBcl-2) was constructed employing the two-plasmid homologous recombination method of Graham (4). Plasmid pcDNA3-hBcl-2 (provided by Dr. Reed, La Jolla Cancer Research Foundation, La Jolla, Calif.) was used as a source of the human Bcl-2 gene. Full-length hBcl-2 was excised from the plasmid pcDNA3-Bcl-2 with EcoRI and XhoI to release 0.7 kb fragment containing hBcl-2 ORF, and then subcloned into the EcoRI and XhoI site of the shuttle plasmid pCA13 (Microbix, Inc., Ontario, Canada). The resultant plasmid, pCAhBcl-2, sequentially contains 0.5 map units of sequence from the left end of the adenovirus 5 (Ad5) genome, cytomegalovirus promoter, the human Bcl-2 gene, a unique ClaI site, followed by SV40 poly(A) signal sequences. Restriction endonuclease digestion and direct sequence analysis confirmed the orientation and sequence of the inserted hBcl-2. The resultant plasmid, pCAhBcl-2 was then co-transfected into the adenoviral packaging cell line 293 together with the adenoviral packaging plasmid pJM17 (Microbix, Inc., Ontario, Canada) employing Lipofectin (BRL, Gaithersburg, Md.). After co-transfection, cells were overlaid with Dulbecco's modified Eagles Media/F12 (Mediatech/Cellgro) supplemented with 2.5% heat-inactivated fetal bovine serum (FBS) (Hyclone Lab, Logan, Utah) and 0.65% noble agar (DIFCO Lab, Detroit, Mich.). Individual plaques of AdCMVhBcl-2 were picked approximately 10 days post-transfection and carried through three additional isolation steps. The virus was then purified using equilibrium centrifugation in CsCl gradient. To prove the identity of AdCMVhBcl-2, its genomic DNA was subjected to restriction enzyme analysis. In addition, PCR utilizing a pair of primers designed to amplify E1A region of adenoviral genome was utilized to test DNA isolated from CsCl-purified virions of AdCMVhBcl-2. In addition, the presence of the expression cassette in the viral genome was confirmed by DNA sequencing. The number of particle forming units per preparation was determinated by plaque assay. The possible contamination of the viral preparation by spontaneously generated replication competent adenovirus (RCA) was eliminated by plaque assay on HeLa cells.

A similar recombinant adenovirus encoding the reporter gene Luciferase (AdCMVLuc) or E. coli β-galactosidase (AdCMVLacZ) was used as a control and for the transfection efficiency studies.

EXAMPLE 4
Neonatal Porcine Islet Isolation

Piglets were anesthetized with Halotane and subjected to laparotomy. The pancreas was then dissected carefully from surrounding tissue and placed in cooled (4° C.) HBBS (Gibco) supplemented with 0.25% BSA (fraction V, Sigma Chemical Co., St. Louis, Mo.), 10 mM/liter Hepes (ICN Biomedicals, Inc., Costa Mesa, Calif.), 100 U/ml penicillin, and 0.1 mg/ml streptomycin. The pancreas was cut into small fragments and transfered into sterile tubes containing HBSS with 2.5 mg/ml collagenase, and agitated for 15 minutes in a shaking water bath at 37° C. The digest was filtered (nylon screen 500 mm), washed four times in HBSS and then placed in bacteriological petri dishes containing Ham's F10 tissue culture medium supplemented with 10 mM/liter glucose, 50 mM/l IBMX, 0.5% BSA, 2 mM/l L-glutamine, 10 mM/l nicotinamide, 100 U/ml penicillin, and 100 mg/ml streptomycin. Korbutt et al. showed that the majority of the neonatal islet cell aggregates after isolation are exocrine cells, however, by day 9 post-isolation, <5% of the cells are identified as exocrine.

EXAMPLE 5
Liver Procurement, Preservation and Rewarming

Forty-eight hours after adenovirus administration, liver procurement was performed following standard microsurgical techniques for mice liver transplantation. Briefly, animals were anesthetized with ketamine and xylazine, the peritoneal cavity was opened by a transverse abdominal incision at the level of the xyphoid process and the liver was freed from its ligaments with minimal manipulation. A 24-gauge catheter was inserted into the portal vein and secured with a 6-0 silk suture. The liver was flushed with 15 ml of UW solution, at 4° C., 10–12 cm of water while the suprahepatic and infrahepatic vein cava were transected to allow venting of the flushing solution. Duration of the organ procurement of the liver was <5 minutes. The liver grafts were placed in individual sterile plastic sample bags (Fisherbrand #01-815-21), and immersed in 50 ml of UW, at 4° C. for 0, 24 and 48 hours. To induce additional liver injury, liver grafts were rewarmed at 37° C. for 60 minutes after 48 hours of cold preservation time.

EXAMPLE 6
In vivo Gene Transfer

Adenovirus-mediated gene transfer to the liver was carried out after tail vein injection of $1\times10^9$ pfu of AdCMV-LacZ or AdCMVBcl-2 48 hours before the I/R-injury. Three experimental groups were evaluated: Group 1 (n=8) animals received intravenous injection of PBS alone, Group 2 (n=8) animals received a recombinant adenovirus vector encoding a reporter gene (AdCMVLacZ) and Group 3 (n=8) animals received AdCMVhBcl-2.

EXAMPLE 7
In vitro Adenoidal Gene Transfer

HUVEC's transfection was performed when cells reached 100% confluence. Different multiplicity of infection per cell were allowed to proceed for two hours in OptiMEM culture media containing 2% FBS, followed by incubation for 24 hours in 199 Medium supplemented with 20% of FCS. Uninfected HUVEC's were used as controls and maintained and processed in a similar way.

EXAMPLE 8
Gene Transfer and Islet Culture

Nine days after the isolation, 300 islets aggregates were plated air in 24 well plates (A/2; Costar, Cambridge, Mass.) containing Ham's F10 tissue culture medium (supplemented as described above) and maintained at 37° C. in 5% CO2 95%. Gene transfer was performed in OptiMEM medium in a minimum volume of 0.5 mL. After 2 hours, Ham's F10 was added and after overnight infection, the cells were washed (3×) with Hank's balanced solution. The medium and well plates were changed every second day thereafter. Islet morphology was assessed daily under an inverted microscope. Non-transfected neonatal porcine islets were processed in parallel with similar conditions without adenoviral infection. Gene transfer was performed with adenovirus vectors at various (10, 50, 100, 500 and 1000) particle forming units (pfu)/cell.

EXAMPLE 9
Expression of Bcl-2 in the Liver Grafts by RT-PCR

The total RNA was extracted from snap-frozen liver biopsies using an RNA STAT-60 kit (Tel-Test "B", Inc. Friendswood, Tex.) according to the manufacturer's recommendations. Briefly, after homogenization in RNA STAT-60 (1 ml/50 mg tissue), the samples were incubated for five minutes at room temperature to allow dissociation of nucleoprotein complexes. Next, 0.2 ml of chloroform per ml of RNA STAT-60 was added. After 2–3 minutes at room temperature, the samples were centrifuged at 12,000 g for 1.5 minutes at 4° C. RNA was precipitated with isopropanol at −70° C. overnight, washed in 70% ethanol and resuspended in RNase-free water. The first-strand cDNA synthesis was catalyzed by Molone Murine Leukemia Virus reverse transcriptase with 15 μg of total RNA and used random hexamers primers. The First-Strand cDNA Synthesis Kit (Pharmacia Biotech, Inc. Milwaukee, Wis.) was used according to the manufacturer is recommendations. The cDNA was then employed as a template for PCR amplification to generate human Bcl-2-specific fragment (~590 bp) using the primers AGTGGGATGCGGGAGATGTG (SEQ ID No. 1) and GGGGCCGTACAGTTCCACAA (SEQ ID No. 2).

EXAMPLE 10
Transfection Efficiency in HUVEC's

To assess the transfection efficiency of adenoviral vectors in HUVEC's, (AdCMVLacZ) was used as a reporter gene. Adenoidal infection with AdCMVLacZ were performed at multiplicities of infection of 100, 500, and 1000 pfu/cell. LacZ expression was monitored using the FACS-Gal method as previously described (5). This assay measures β-galactosidase activity in individual viable eukaryotic cells. Enzyme activity is measured by flow cytometry, using the fluorogenic substrate fluorescein di-β-D-galactopyranoside (FDG), which is hydrolyzed and retained intracellularly. After adenoviral infection cells were harvest and analyzed for expression of encoded reporter gene to assess the relative efficiency of gene transfer. Briefly, 48 hours after viral infection the cells were resuspended in staining media (SM) (10 mM HEPES, and 4% FCS in 1×PBS, pH 7.3). Cells were then spun at 5,000 rpm for 5 minutes and incubated for 15 min in blocking buffer (10% NMS in 1×PBS). Then, cells were washed once, resuspended in 50 ml of SM, and incubated in a 37° C. water bath for 5 min. 50 ml of SM containing 2 mM FDG (Sigma, St. Louis, Mo.) was mixed thoroughly with the cells in hypotonic conditions, and the cells were returned to the water bath for exactly 1 minute. FDG loading was stopped by adding 500 ml of ice-cold SM. Cells were maintained in ice until the FACS analysis was performed approximately 30 minutes later. FACS analysis (Flow Analysis and Cell Sorting) was performed in $1\times10^4$ events in a pool of cells from duplicate experiments, and data was expressed as a number of fluorescent cells. Percentage of cells within each region was calculated using the CellFIT program version 1.0 (Becton Dickinson).

EXAMPLE 11
Liver Function Test

Blood samples for aspartate amino transferase (AST) and alanine amino transferase (ALT), and lactate dehydrogenase (LDH) levels were obtained after 6 hours of reperfusion, and were analyzed using a serum analyzer (Amos Seralyzer, Miles Inc, Diagnostics Division, Elkhart, Ind., USA).

EXAMPLE 12
Liver Morphologic Assessment

Liver biopsies for histological assessment were obtained both before ischemia, and 6 hours following the reperfusion. Liver specimens were fixed in 10% formalin and embedded in paraffin. Six-micrometer hematoxylin and eosin (H&E)-stained sections were evaluated at 200× magnification by a point-counting method for severity of hepatic injury using an ordinal scale as previously described (39). Grade 0: minimal or no evidence of injury; grade 1: mild injury consisting in cytoplasm vacuolation and focal nuclear pyknosis; grade 2: moderate to severe injury with extensive nuclear pyknosis, cytoplasmic hypereosinophilia, and loss of intercellular borders; and grade 3: severe necrosis with disintegration of hepatic cords, hemorrhage and neutrophils infiltration.

EXAMPLE 13
Immunoblot Analysis of Human Bcl-2 Protein Expression

HUVEC's were seeded at $2.5 \times 10^5$ cells in six-well plate. After overnight culture, cells were then infected with the AdCMVhBcl-2 recombinant adenoviral vector. As a control, cells were infected with irrelevant adenovirus encoding the Luciferase reporter gene (AdCMVLuc). Infections were allowed to proceed for two hours in OptiMEM culture media containing 2% FBS, followed by incubation for 24 hours in DMEM supplemented with 10% FBS. Uninfected controls, not exposed to viral vectors, were maintained and processed in the same manner. 100 mg of total protein from cellular lysate were size-fractionated by 12% sodium dodecyl sulfate-polyacrylamide (SDS) gel electrophoresis and electroblotted onto a nitrocellulose membrane. The human Bcl-2 protein was detected using the monoclonal antibody mouse anti-human Bcl-2 (Oncogene) at a 1:3,000 dilution, followed by the addition of goat anti-mouse HRP antibody. The membrane was developed with Western blot chemiluminescence reagent (DuPONT NEN, Boston, Md.). As control for equal loading of protein c-myc was also detected. Reference Coomassie-stained gels were also run. The molecular weight of the Bcl-2 is 25 kDa.

EXAMPLE 14
Cold Preservation

Second passage endothelial cells were seeded into six-well plates at an initial seeding density of $2.5 \times 10^5$ cells per $cm^2$. Twenty-four hours after the adenoviral vector infection, cell were washed with phosphate-buffered saline (PBS), and 1.5 ml of cold preservation solution (4° C.) was added and the plates were stored at 4° C. for 48 hours.

EXAMPLE 15
Detection of Apoptosis

A commercial in situ histochemical assay (Klenow-FragEL, Oncogene Research Products, Cambridge, Mass.) was used to detect the DNA fragmentation characteristic of apoptosis. In this assay, Klenow binds to exposed ends of DNA fragments generated in response to apoptotic signals and catalyzes the template-dependent addition of biotin-labeled and unlabeled deoxynucleotides. Biotinylated nucleotides are detected using a streptavidin-horse radish peroxidase conjugate. Diaminobenzidine reacts with the labeled sample to generate an insoluble colored substrate at the site of DNA fragmentation. Counterstaining with methyl green aids in the morphological evaluation of normal and apoptotic cells. The results were scored semiquantitatively by averaging the number of apoptotic cells per microscopic field at 25× magnification. Six fields were evaluated per tissue sample.

DNA fragmentation by ELISA assay was performed to quantify islet apoptosis. DNA fragmentation, the biochemical hallmark of apoptosis, was determined using a sandwich ELISA (Bohringer-Mannheim) which measure cytosolic histone-associated DNA fragments (mono or oligonucleosomes). After lysis of control or transfected whole islets with 0.2% Triton X-100, cytosolic fractions (centrifugation at 20,000 g) of islets were applied to a microtiterplate coated with anti-histone antibody. In a second and third step, anti-DNA antibody and anti-DNA peroxidase were added, respectively. After incubation with peroxidase substrate (2,2'-azinodi-[s-ethylbenzthiazonline sulfonate]), the absorbence of the immunocomplex was photometrically determined at 405 nm against substrate solution alone (blank). Results were expressed as enrichment factor (EF), which represents the ratio of optical densities for control.

EXAMPLE 16
Islet Transplantation

After 7 days in culture, approximately 500–700 islet were transplanted intraperitoneally in SCID mice. No immunosuppression was given. Glucose (0.5 mg/g of body weight) stimulated insulin secretion was assessed 4 and 8 weeks after transplantation. All data is expressed as a mean±SEM. Treatment groups were compared statistically using unpaired two-tailed Student's test. The Kaplan Meier method was used to plot the survival distributions of each group. The LogRank Test was used to compare the survival distributions of the groups.

Figure 2A:
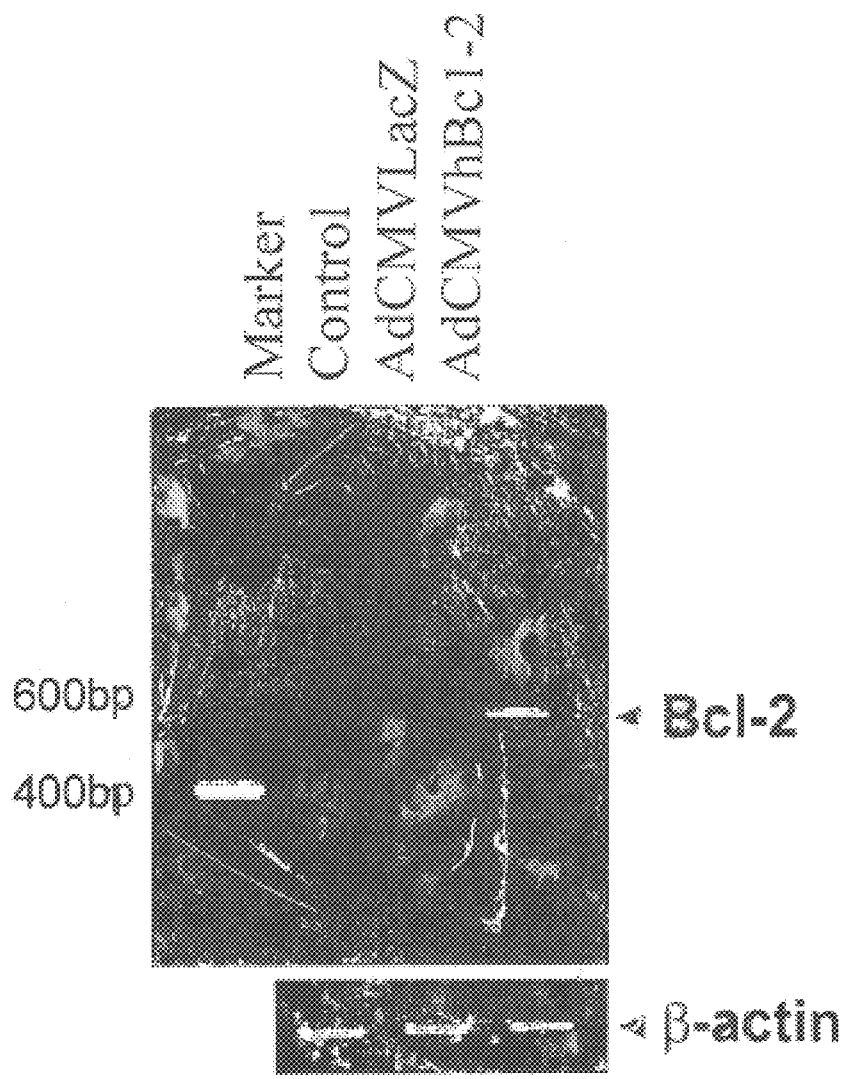
FIG. 2A shows expression of the hBcl-2 gene in the liver 48 hours after in vivo gene transfer with AdCMVhBcl-2 analyzed by RT-PCR.

EXAMPLE 17
Generation of a Recombinant Adenovirus Vector Encoding the Human Bcl-2 Gene and Expression of Human Bcl-2 in the Liver A recombinant adenovirus vector encoding (AdCMVhBcl-2) the human Bcl-2 gene driven by the CMV promoter was generated (FIG. 1). AdCMVhBcl-2 was able to cytoprotect human endothelial cells and liver grafts in hypothermia during standard preservation time for organ transplantation. AdCMVhBcl-2 was first demonstrated to mediate transfer of the Bcl-2 gene to the liver. To this end, mice were injected intravenously (IV) with AdCMVhBcl-2, with a control vector expressing the $E$ $coli$ β-galactosidase gene AdCMVLacZ, or with phosphate buffered saline (PBS) alone. At 48 hours post-injection, total RNA was extracted from the livers and subjected to RT-PCR. As shown in FIG. 2A, expression of the Bcl-2 gene could be detected in the liver of mice injected with AdCMVhBcl-2, but not in the liver of mice injected with the control vector or PBS. High levels of Bcl-2 were obtained 8 hours after IV AdCMVhBcl-2 administration. Intravenous administration of adenoviral vectors, $1 \times 10^9$ pfu, transduces>95% of hepatocytes with 20–40 viral genome copies per cell (Vrancken Peeters, et al., 1996; Vrancken Peeters, et al., 1996). No detection of Bcl-2 or other reporter genes has been detected in other organs. Thus, Bcl-2 expression in the liver can be accomplished in vivo after systemic administration of a recombinant adenovirus encoding Bcl-2.

EXAMPLE 18

Figure 3:
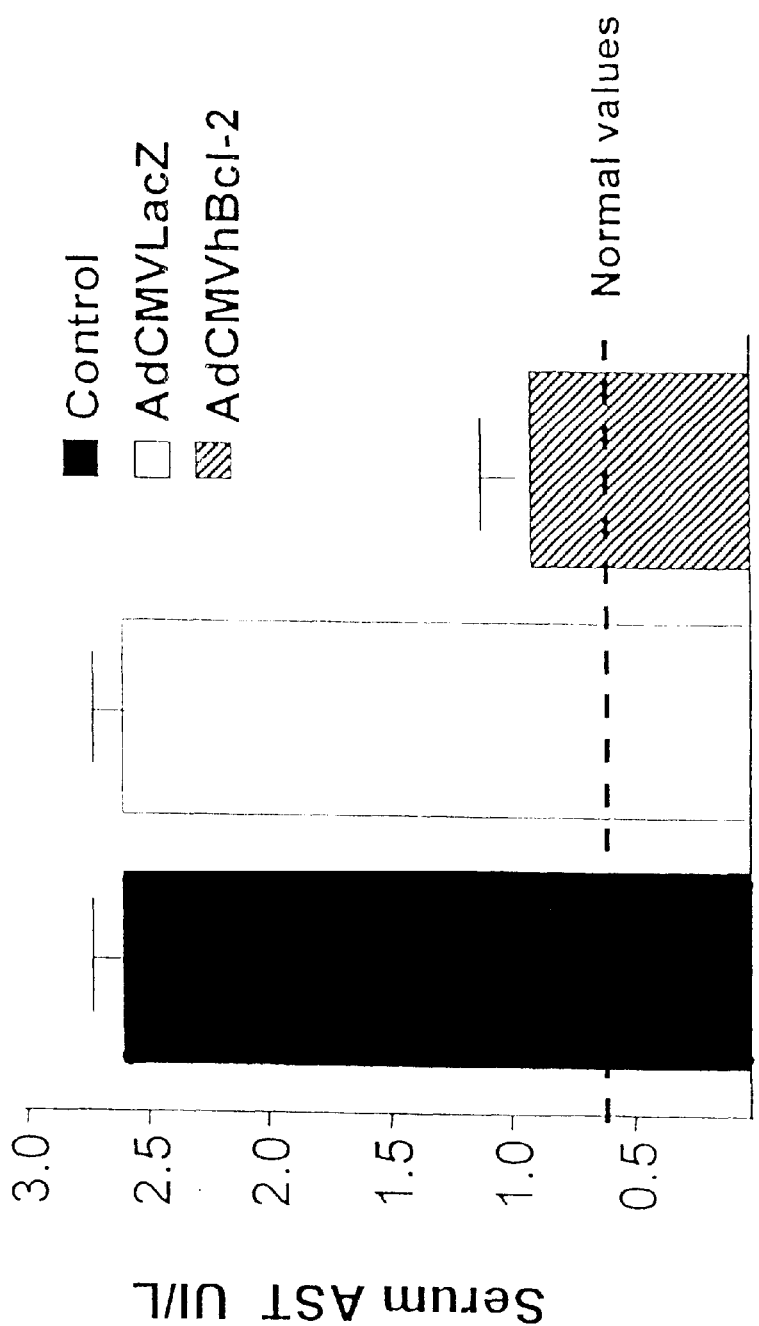
FIG. 3 shows reduced aspartate amino transferase levels after ischemia/reperfusion-injury to the liver in animals injected with AdCMVhBcl-2.
Figure 4:
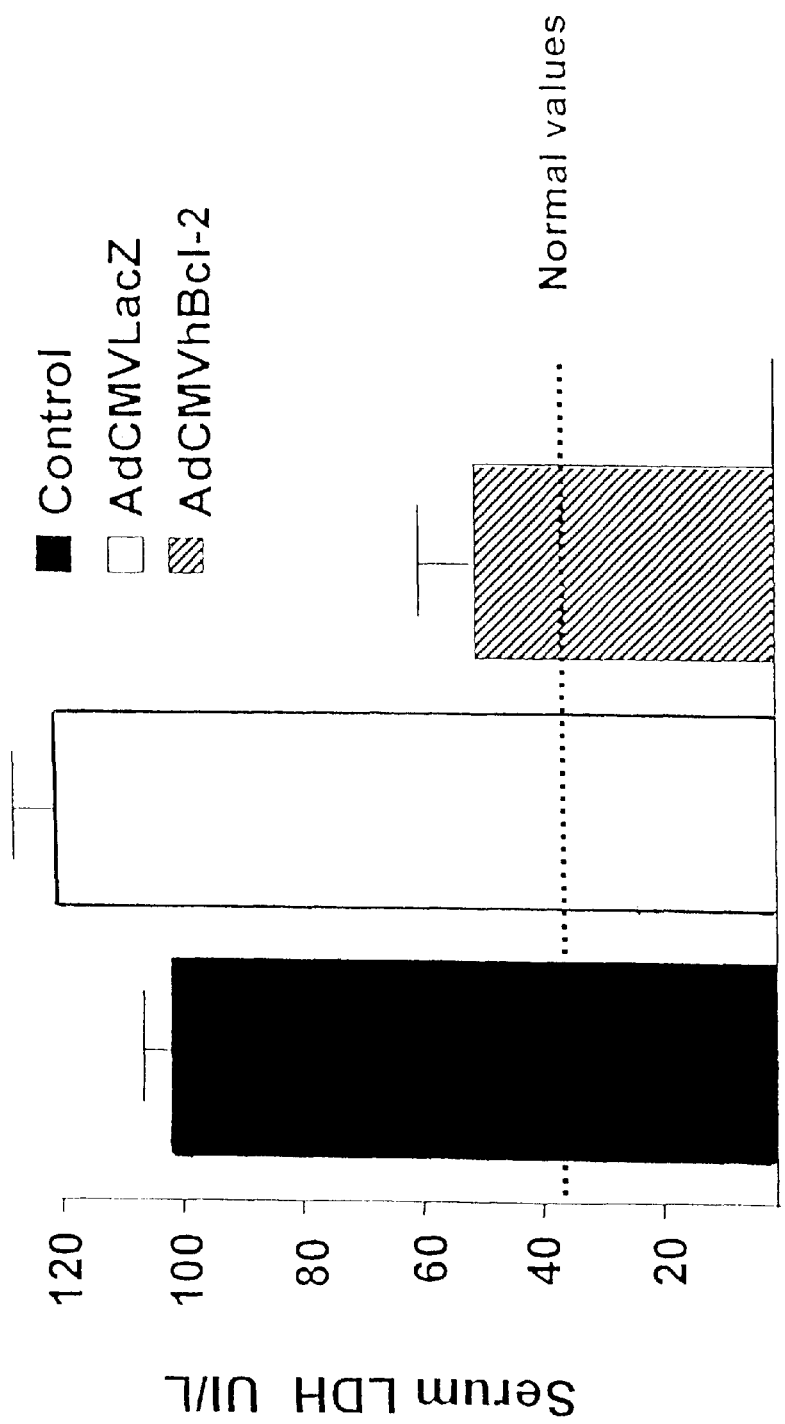
FIG. 4 shows reduced lactate dehydrogenase levels in animals cytoprotected with AdCMVhBcl-2 after ischemia/reperfusion-injury to the liver.

Reduced Ischemia-Reperfusion Injury in Livers Transfected With the Anti-Apostolic hBcl-2 Gene Having confirmed that IV injection of AdCMVhBcl-2 led to expression of the anti-apoptotic Bcl-2 gene in the liver, the next investigated was whether this could induce cytoprotection after I/R-injury of the liver. Mice were injected IV with AdCMVhBcl-2, the control vector AdCMVLacZ, or with PBS. For these studies, a previously described model of segmental hepatic warm ischemia was employed (Camargo, et al., 1997). I/R-injury was induced by occlusion of the median lobe of the liver (approximately 45% of the liver mass) for 30–40 minutes. Measuring serum aspartate amino transferase (AST) and alanine amino transferase (ALT) levels assessed liver injury in the 3 experimental groups. AST is an established marker of hepatic damage after warm ischemia and reperfusion injury (Camargo, et al., 1997; Iu, et al., 1987). Preliminary studies showed that the peak of aspartate amino transferase concentration in animals subjected to 30–40 minutes of ischemia of 45% of the liver mass occurs between 5–7 hours post-injury (data not shown). The serum aspartate amino transferase levels were measured 6 hours post-injury. Animals from the control group injected with PBS showed a significant increase in serum aspartate amino transferase levels 6 hours after the I/R-injury (FIG. 3). Animals injected with an adenovirus vector encoding an irrelevant gene (AdCMVLacZ) showed a similar increase in aspartate amino transferase levels. In contrast, animals infected with the AdCMVhBcl-2 vector showed a significant reduction in aspartate amino transferase. An increase in aspartate amino transferase was observed in animals treated with AdCMVLacZ followed by sham operation (1.3±0.2 UI/L) compared with PBS (0.6±0.2 UI/L) or AdCMVhBcl-2 (0.8±0.22 UI/L). This reflects the hepatotoxic effect of adenovirus vectors as reported (Gao, et al., 1996; Jooss, et al., 1996). Serum aspartate amino transferase levels followed a similar pattern. A significant reduction of the LDH peak 6 hours after the I/R-injury was observed in animals infected with AdCMVhBcl-2 (FIG. 4). These results demonstrate that adenovirus-mediated gene transfer of the anti-apoptotic Bcl-2 gene induces hepatoprotection against I/R-injury of the liver and to adenoviral vectors.

EXAMPLE 20

Histological Analysis After I/R-Injury

Figure 5:
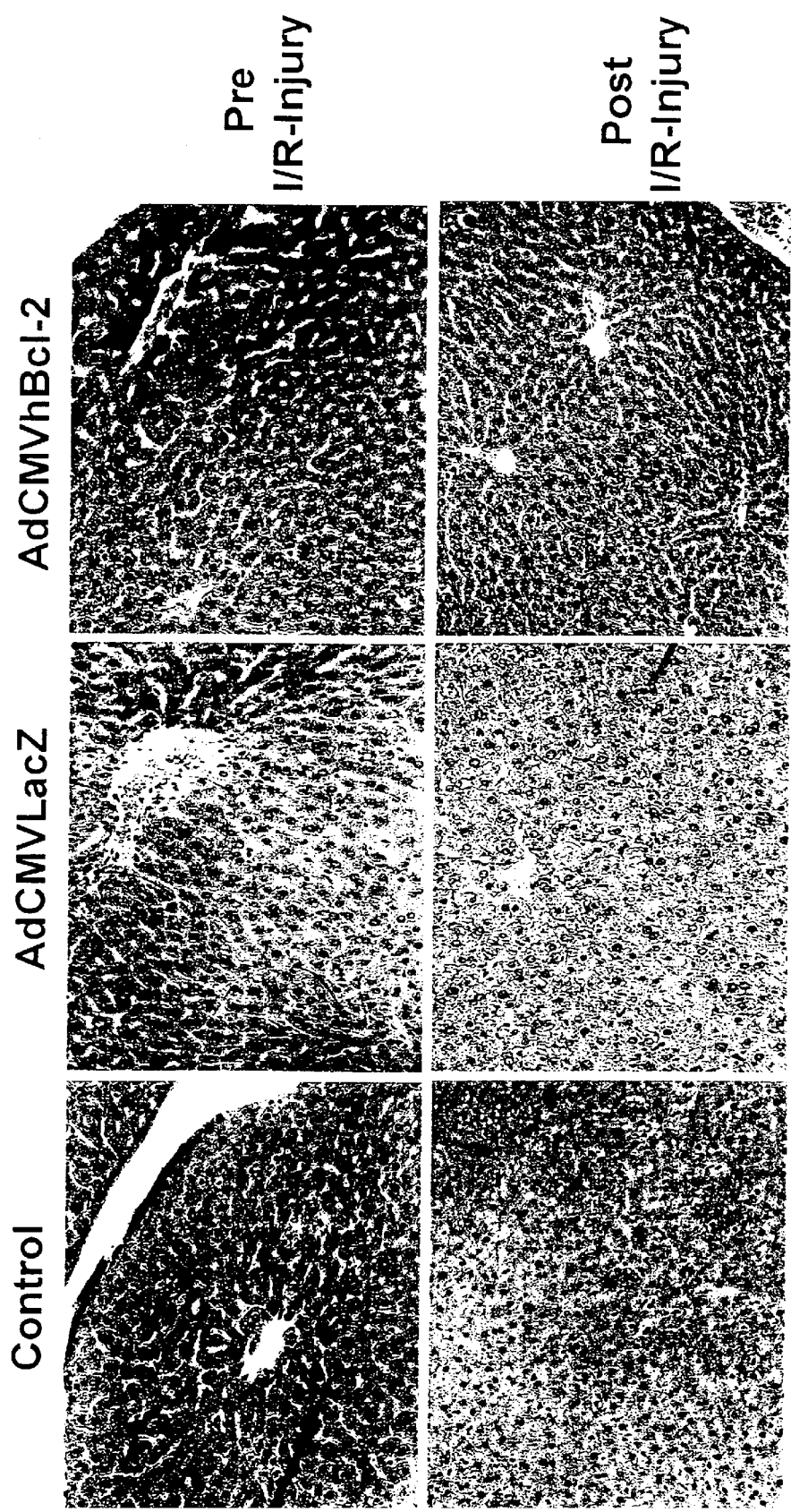
FIG. 5 shows histological analysis after ischemia/reperfusion-injury to the liver.

Next investigated was the degree of hepatocyte injury in this experimental model. To this end, hematoxilin and eosin (H&E) stained biopsies were subjected to a point-counting method using an ordinal scale as described (Camargo, et al., 1997). Liver specimens obtained 6 hours after the I/R-injury (median lobe of the liver) from control animals injected with PBS or the irrelevant vector, AdCMVLacZ showed moderate to severe injury (Grade 2–3) with nuclear pyknositosis, cytoplasmic hypereosinophilia, and loss of intercellular borders. Areas of necrosis with disintegration of hepatic cords and neutrophils infiltration were also evident (FIG. 5). Consistent with the levels of transaminases, animals injected with AdCMVBcl-2 showed minimal evidence of injury including a significant reduction of liver necrosis (Grade 0–1). Mild neutrophilic infiltrate and apoptotic degeneration of hepatocytes was evident before the ischemic injury in samples obtained 48 hours after AdCMVLacZ administration. These morphologic alterations have been previously reported and represent an inflammatory response to the adenovirus vectors after intravascular administration (Gao, et al., 1996; Jooss, et al., 1996). Interestingly, livers infected with AdCMVhBcl-2 showed no significant difference before the ischemic injury compared with control animals treated with PBS. These results suggest that Bcl-2 might protect the host cell against the cytotoxic effects of the adenovirus vector or decrease the inflammatory response secondary to the viral infection.

EXAMPLE 21

Reduced Apoptosis of the Liver Parenchyma Cells After I/R-Injury In Animals Treated With Bcl-2

Figure 6:
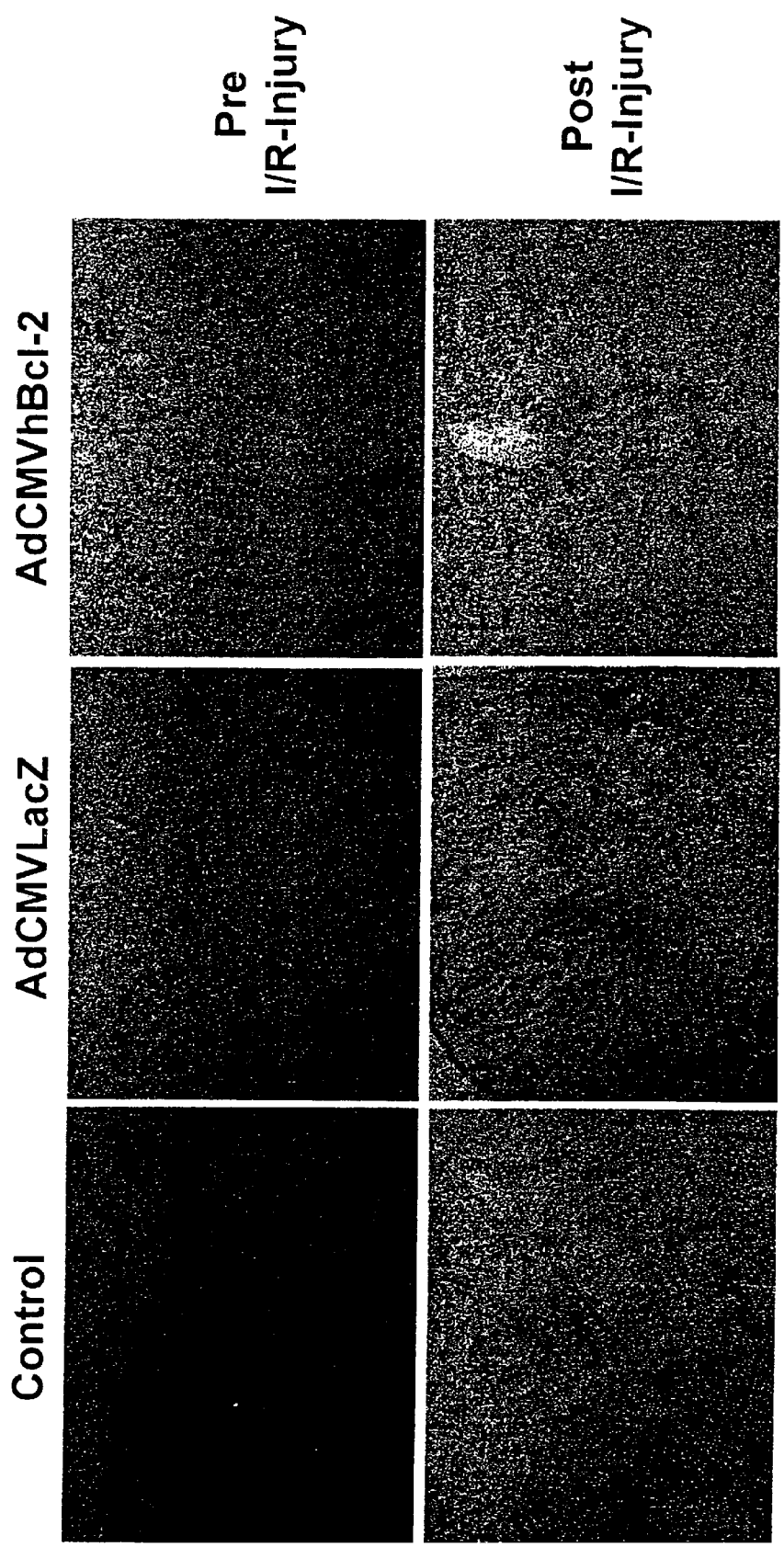
FIG. 6 shows apoptosis of the liver parenchyma cells after ischemia/reperfusion-injury.

Having demonstrated that Bcl-2 protects the liver against ischemia/reperfusion-injury, whether this was the result of reduced apoptosis in the liver parenchyma cells was examined. To investigate this, an in situ histochemical assay was employed to detect the DNA fragmentation characteristic of apoptosis. Apostolic cells were more evident in post-reperfusion samples from animals injected with PBS or with adenovirus carrying an irrelevant gene (Table 1 and FIG. 6). In contrast, significant less number of apoptotic cells were present in the animals treated with the AdCMVhBcl-2 (p=<0.01). Samples from animals treated with AdCMVLacZ showed a higher number of apoptotic cells before the ischemic injury compared with AdCMVhBcl-2 injected animals. Thus, the results demonstrated the ability of Bcl-2 to protect the host cell against the cytotoxic effects of the adenovirus vectors.

TABLE 1

Reduced Incidence of Apoptosis Cells after Reperfusion in Animals Injected with AdCMVhBcl-2

|  | Control | AdCMVLacZ | AdCMVhBcl-2 |
| --- | --- | --- | --- |
| Pre-I/R-Injury | 2.3 ± 2 | 17.5 ± 5$^a$ | 1.41 ± 2$^a$ |
| Post-I/R-Injury | 42.4 ± 15$^b$ | 64.2 ± 18$^b$ | 8.7 ± 4$^b$ |

Liver samples were sectioned and subjected to DNA fragmentation detection analysis. Random sections from each tissue groups were evaluated by counting the number of Klenow+cells (25×magnification). Results: mean±SEM of positive cells/field/6 fields per tissue. $^a$ p<0.01 vs. AdCMVLacZ only. $^b$ p<0.001 vs. Control and AdCMVLacZ

EXAMPLE 22

Prolonged Survival After I/R-Injury to the Liver In Animals Genetically Modified in vivo With AdCMVBcl-2

Figure 7:
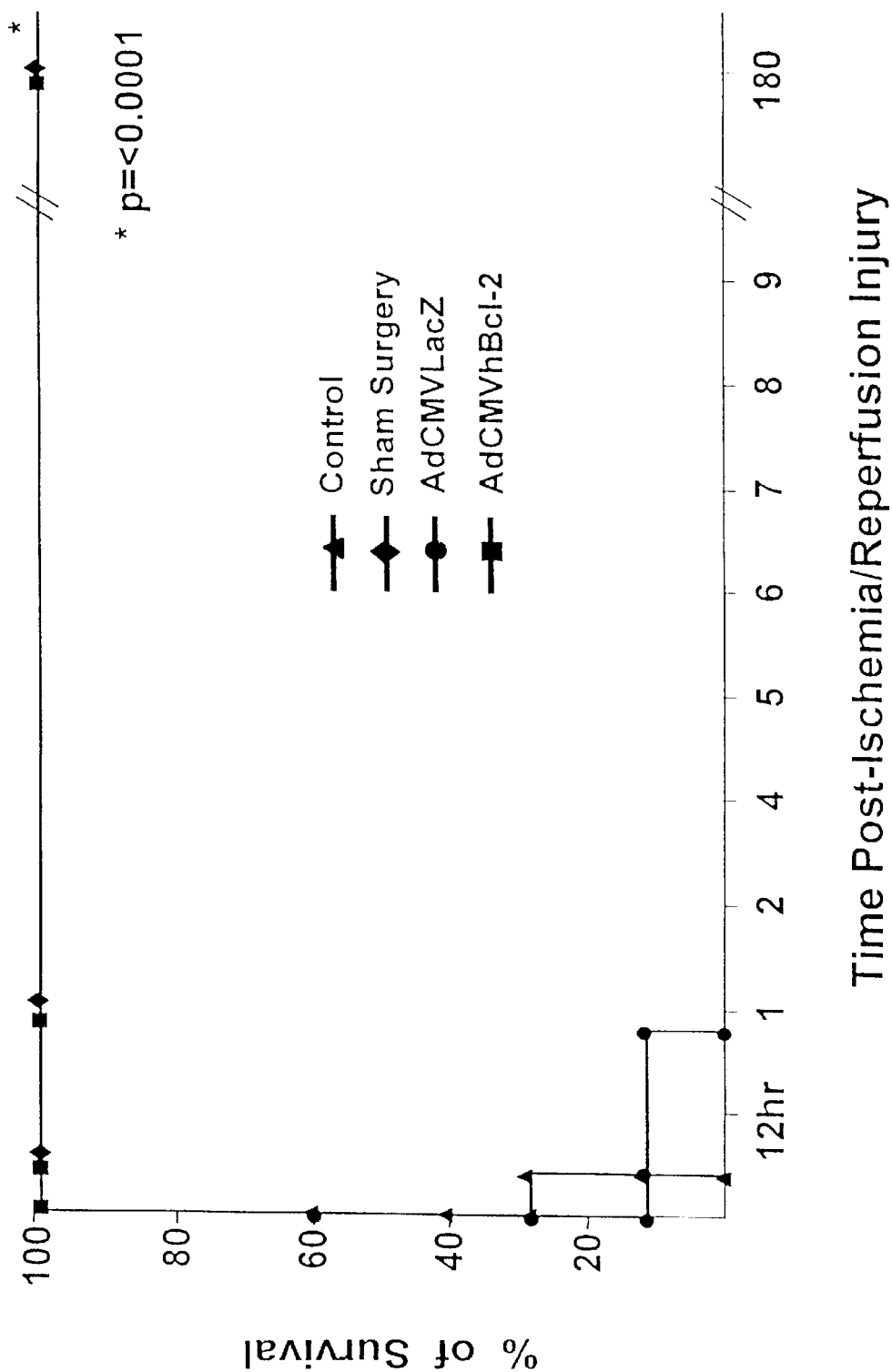
FIG. 7 shows prolonged survival after ischemia/reperfusion-injury to the liver in animals genetically modified in vivo with AdCMVhBcl-2.

Whether the cytoprotective effect of the anti-apoptotic Bcl-2 gene would translate into a survival advantage in animals with ischemia/reperfusion-injury was determined next. Animals were injected with AdCMVhBcl-2, AdCMVLacZ or PBS and then subjected to ischemia/reperfusion-injury. For these studies, the superior mesenteric artery was occluded for 20–30 minutes. Preliminary studies showed that the mortality of normal mice with 20–30 minutes of SMA occlusion is 97% at 24 hours. Moreover, serum AST and ALT levels increased significantly and histological examination demonstrated extensive hepatocellular damage. The survival after 24 hours of control animals injected with PBS was zero and only 20% of animals treated with AdCMVLacZ survived this length of time. However, all of the animals treated with AdCMVBcl-2 survived indefinitely (p=<0.0001) (FIG. 7). All of mice in the sham operated group survived, which excludes the anesthetic procedure as the direct cause of death in this experimental model. Sixth months later, four survivors were sacrificed for histological analysis and western blot studies for Bcl-2 protein expression, no expression of Bcl-2 was observed. In this regard, no evidence of malignant transformation was observed in pathology analysis of different organs including the liver. The other 4 survivors are currently alive and in perfect condition after 8 months, with normal aspartate amino transferase and ALT plasma levels. Thus, this results show that Bcl-2 confers a significant survival advantage after ischemia/reperfusion-injury to the liver.

EXAMPLE 23

Figure 9:
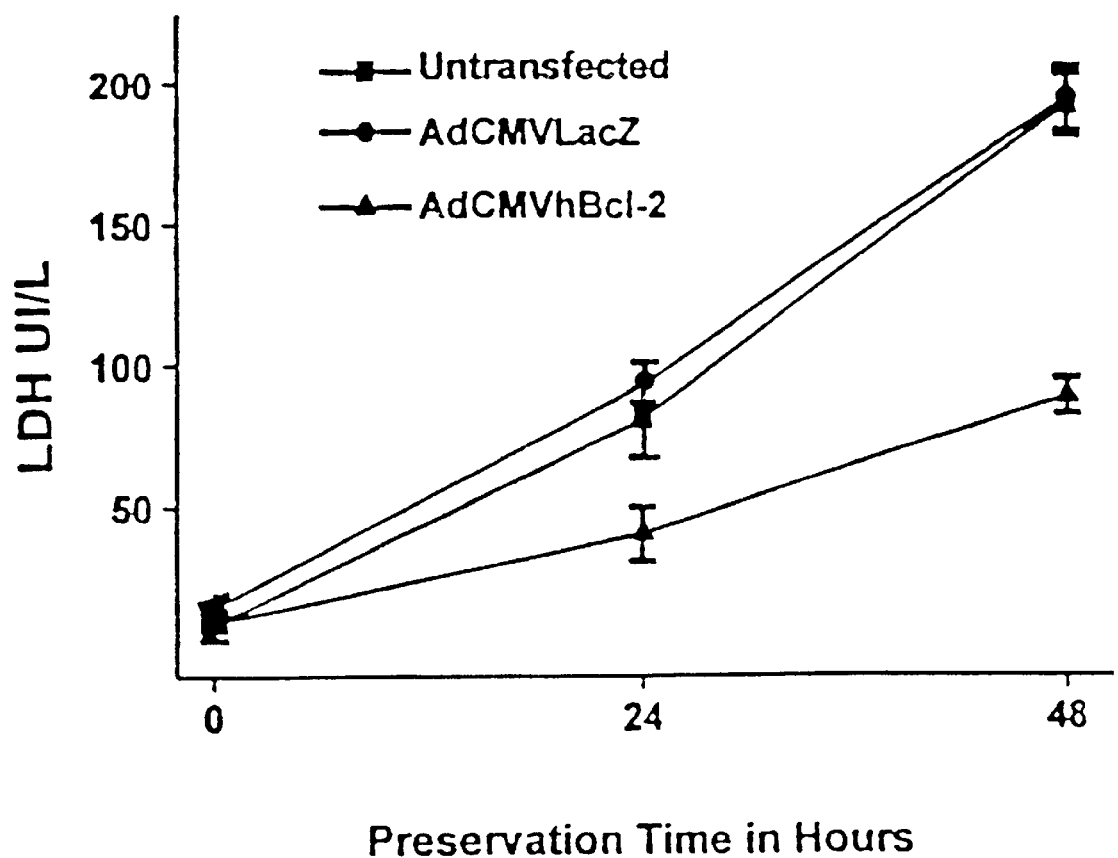
FIG. 9 shows decrease of lactate dehydrogenase release in the preservation solution in animals cytoprotected with hBcl-2. LDH levels were evaluated in the preservation solution after 24 and 48 hours. Significant difference was demonstrated after 48 hours between livers genetically modified with AdCMVhBcl-2 ($1\times10^9$ pfu) compared with controls and AdCMVLacZ treated animals ($P<0.05$). Results are expressed as a mean±SEM.

Genetic Modification of Liver Grafts With an Adenovirus Encoding Bcl-2 for Improved Organ Preservation
Expression of hBcl-2 In Genetically Modified Grafts The expression of hBcl-2 was confirmed in biopsies taken 48 hours post in vivo gene transfer by RT-PCR (FIG. 2A). Analysis of the transfected livers by RT-PCR confirmed the expression of hBcl-2 in the AdCMVhBcl-2 group. In addition, no expression of hBcl-2 was demonstrated in control or AdCMVLacZ groups. High levels of hBcl-2 were observed 12 hours after intravenous adenoviral vector administration. Expression of hBcl-2 protein by immunohistochemical staining in the liver from controls, AdCMVLacZ-, and AdCMVhBcl-2-treated animals is duces >95% of hepatocytes with 20 to 40 viral genome copies per cell (Vrancken Peeters, et al., 1996; Vrancken Peeters, et al., 1996). Higher concentration of AdCMVhBcl-2 do not significantly increased the cytoprotective effect (Table 2). Significant hepatotoxic effect was observed with $1 \times 10^{10}$ pfu of AdCMVlacZ, probably related to the 3-cytopathic effect of the virus on the host cell. These toxic effects were not observed in liver grafts transfected with a high dose of AdCMVhBcl-2. ALT activities followed a similar pattern during the preservation time with significant reduction in the ALT release in grafts genetically modified with AdCMVhBcl-2. LDH activity has also been evaluated as an indicator of liver viability and has been observed less closely related to post-transplant graft function than aspartate amino transferase. LDH levels were examined in all liver grafts and the results are shown in FIG. 9. Like the other hepatocellular enzymes tested, an increase in LDH activity was observed during the preservation. Again, livers cytoprotected with hBcl-2 shown less release compared with grafts from the control groups. Thus, these results showed that the livers cytoprotected with hBcl-2 release less hepatocellular enzymes into the preservation fluid and indicate better preservation condition.

TABLE 2

Cytoprotection of Liver Grafts by Different Doses of AdCMVhBc1–2[a]

| Group | 0 hr | | 24 hr | | 48 hr | | Rewarming | |
|---|---|---|---|---|---|---|---|---|
| | AST | LDH | AST | LDH | AST | LDH | AST | LDH |
| Control | 1.4 ± 0.8 | 12.9 ± 2 | 2.1 ± 0.9[b] | 86.2 ± 8.6[b] | 7.5 ± 2.2[b] | 192 ± 5.3[b] | 30.2 ± 7.5[b] | 302 ± 22[b] |
| AdCMVLacZ 1 × 10$^9$ | 1.2 ± 1 | 16.3 ± 3.1 | 2.4 ± 1.4 | 94.3 ± 4.8 | 7.8 ± 2.8 | 198.2 ± 4.8 | 27.9 ± 8.5 | 330.3 ± 24.5 |
| AdCMVLacZ 1 × 10$^{10}$ | 1.1 ± 0.6 | 14.7 ± 2.4 | 4.6 ± 0.5[c] | 112.2 ± 12[c] | 19.6 ± 1.5[c] | 233 ± 8.1[c] | 57.3 ± 6.1[c] | 365.3 ± 8.3[c] |
| AdCMVBcl–2 1 × 10$^5$ | 1.2 ± 0.9 | 18.6 ± 4.2 | 2.7 ± 0.9 | 92.7 ± 8.6 | 10.7 ± 1.7 | 183.5 ± 9.1 | 36.5 ± 13.1 | 314.7 ± 9.8 |
| AdCMVBcl–2 1 × 10$^6$ | 2 ± 0.9 | 17.6 ± 3.1 | 3 ± 1.4 | 87 ± 1.4 | 10.5 ± 0.7 | 152 ± 5.6[c] | 32 ± 2.8 | 282.2 ± 13.1 |
| AdCMVBcl–2 1 × 10$^7$ | 1.6 ± 0.8 | 16.5 ± 4.2 | 2.2 ± 0.9 | 67.2 ± 3.5[c] | 7.2 ± 1.1 | 132.5 ± 9.1[c] | 23.2 ± 2.7 | 264 ± 7.3[c] |
| AdCMVBcl–2 1 × 10$^8$ | 1.4 ± 0.6 | 16.8 ± 2.2 | 1.7 ± 0.9 | 54.5 ± 4.2[c] | 6 ± 2.5 | 94 ± 5.8[c] | 16.5 ± 2.3[c] | 225 ± 16.3[c] |
| AdCMVBcl–2 1 × 10$^9$ | 0.8 ± 0.9 | 13.3 ± 3.4 | 1.1 ± 1.5 | 41.2 ± 4.9[c] | 1.2 ± 1.3[c] | 82.3 ± 5.2[c] | 9.8 ± 2.1[c] | 198 ± 9.3[c] |
| AdCMVBcl–2 1 × 10$^9$ | 0.9 ± 0.8 | 15.8 ± 2.4 | 1 ± 1.1 | 45.4 ± 6.5[c] | 2.3 ± 0.5[c] | 77.4 ± 6.2[c] | 4.8 ± 3.6[c] | 188.6 ± 7.2[c] |

Figure 2B:
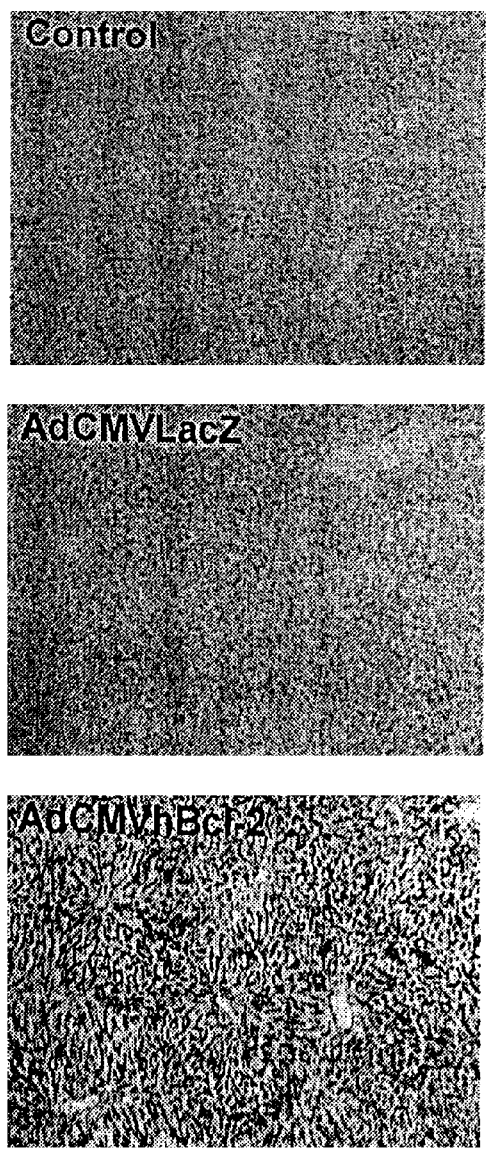
FIG. 2B shows the expression of the hBcl-2 gene in the liver analyzed by immunohistochemical staining.

[a]Results are expressed as a mean ± SEM.
[b]p < 0.05
[c]Student's t test.

shown in FIG. 2B. The majority of hepatocytes (>90%) were shown to express the hBcl-2 protein after systemic administration of $1 \times 10^9$ of AdCMVhBcl-2.

Enzyme Activities In the Preservation Solution

Figure 8:
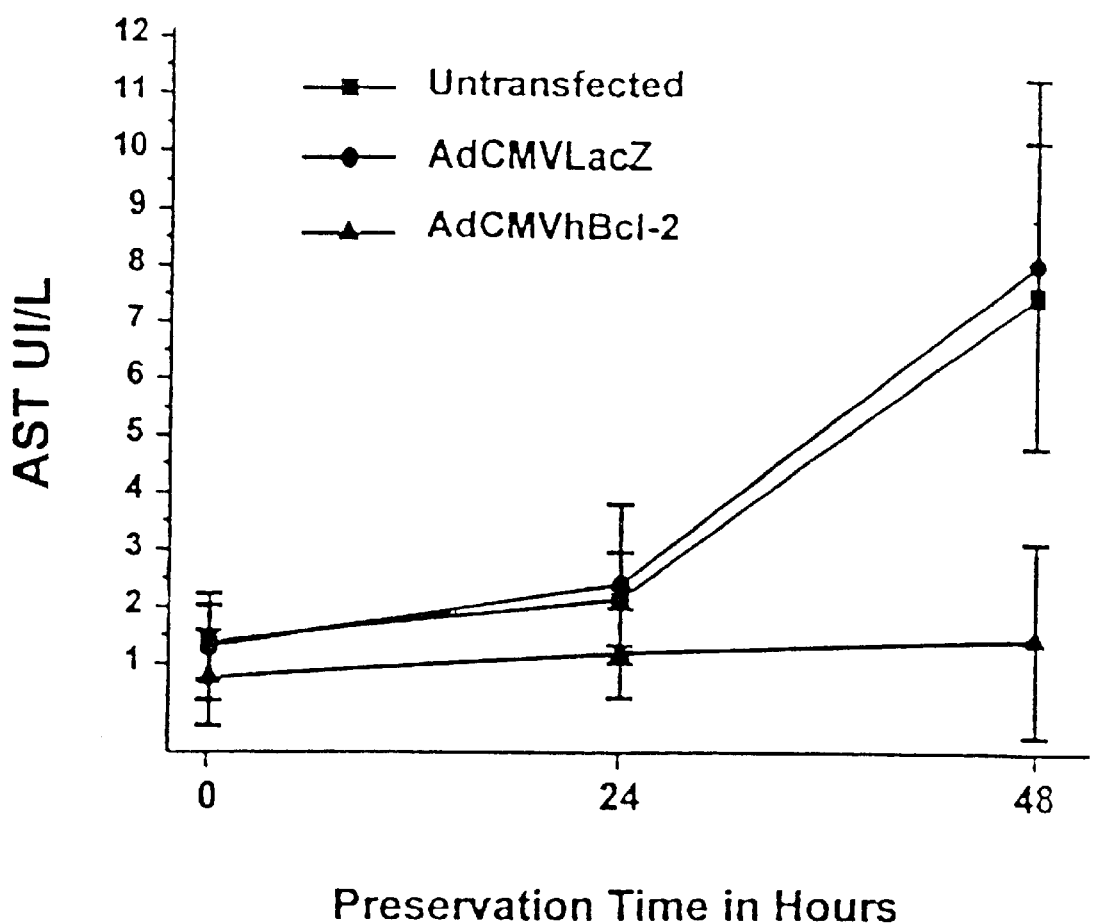
FIG. 8 shows aspartate amino transferase release during liver preservation in UW solution. Aspartate amino transferase activity was analyzed in livers procured from untreated animals, animals transfected with an adenovirus expressing an irrelevant gene (AdCMVLacZ, $1\times10^9$ pfu) and animals treated with AdCMVhBcl-2 ($1\times10^9$ pfu). Significant difference was observed after 48 hours between livers expressing hBcl-2 compared with controls and grafts expressing an irrelevant gene ($P<0.05$). Results are expressed as a mean±SEM.

Determination of changes in the biochemical composition of the solution preserving a donor organ has been demonstrated to be a reliable indicator of graft viability. Significant release of liver-derived enzymes into the preservation fluid has been demonstrated in human liver grafts. Moreover, aspartate amino transferase activity is a discriminative marker of postoperative graft (Devlin, et al., 1995; Hamamoto, et al., 1994). AST release after liver injury induced during the preservation time is demonstrated in FIG. 8. Progressive augmentation of aspartate amino transferase levels were observed in control and AdCMVLacZ grafts with an increase at 48 hours of preservation time. Liver grafts expressing the anti-apoptotic hBcl-2 gene showed a significant decrease in the aspartate amino transferase release during preservation, especially after 48 hours. No differences between groups were observed at 24 hours indicating the high quality preservation obtained experimentally in normal liver grafts in UW solution.

Figure 10:
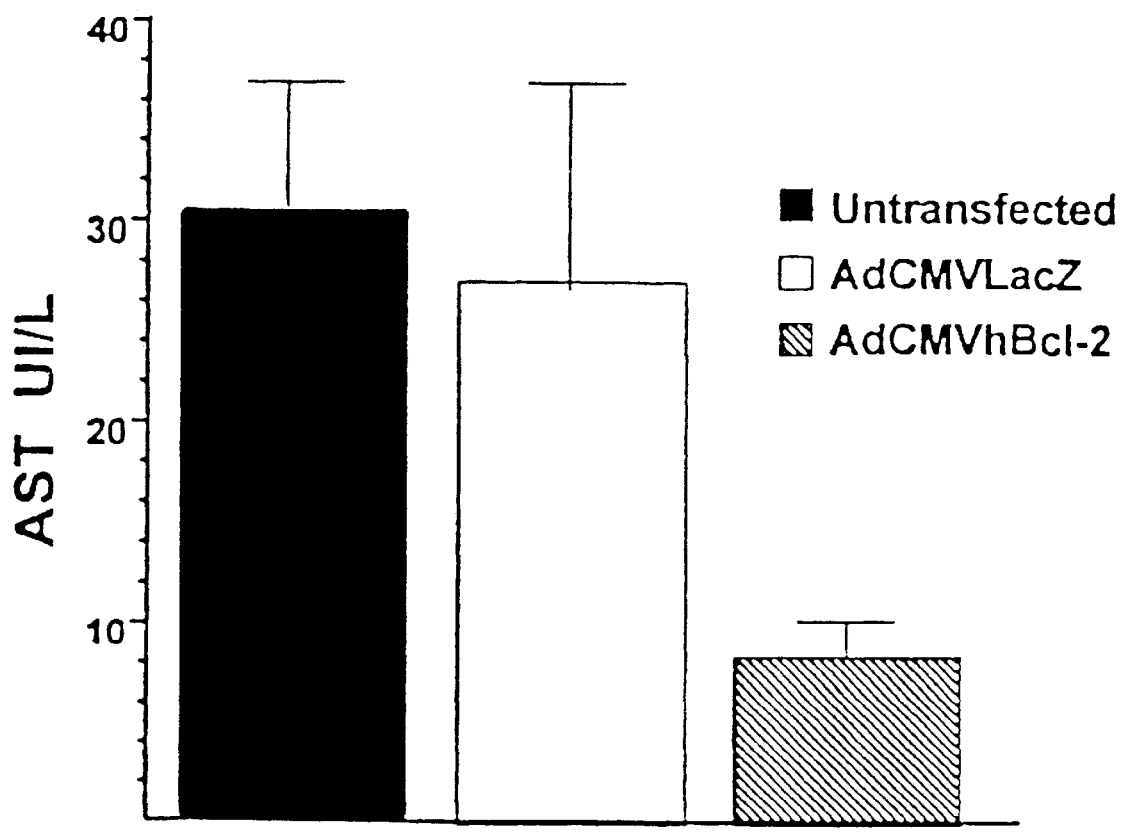
FIG. 10 shows aspartate amino transferase activities in the preservation solution 60 minutes after rewarming at room temperature at the end of the preservation time (48 hours). Liver grafts from untreated animals and animals transfected with AdCMVLacZ ($1\times10^9$ pfu) showed a significant higher aspartate amino transferase release compared with grafts expressing hBcl-2($1\times10^9$ pfu, $P<0.05$). Results are expressed as a mean±SEM.
Figure 11:
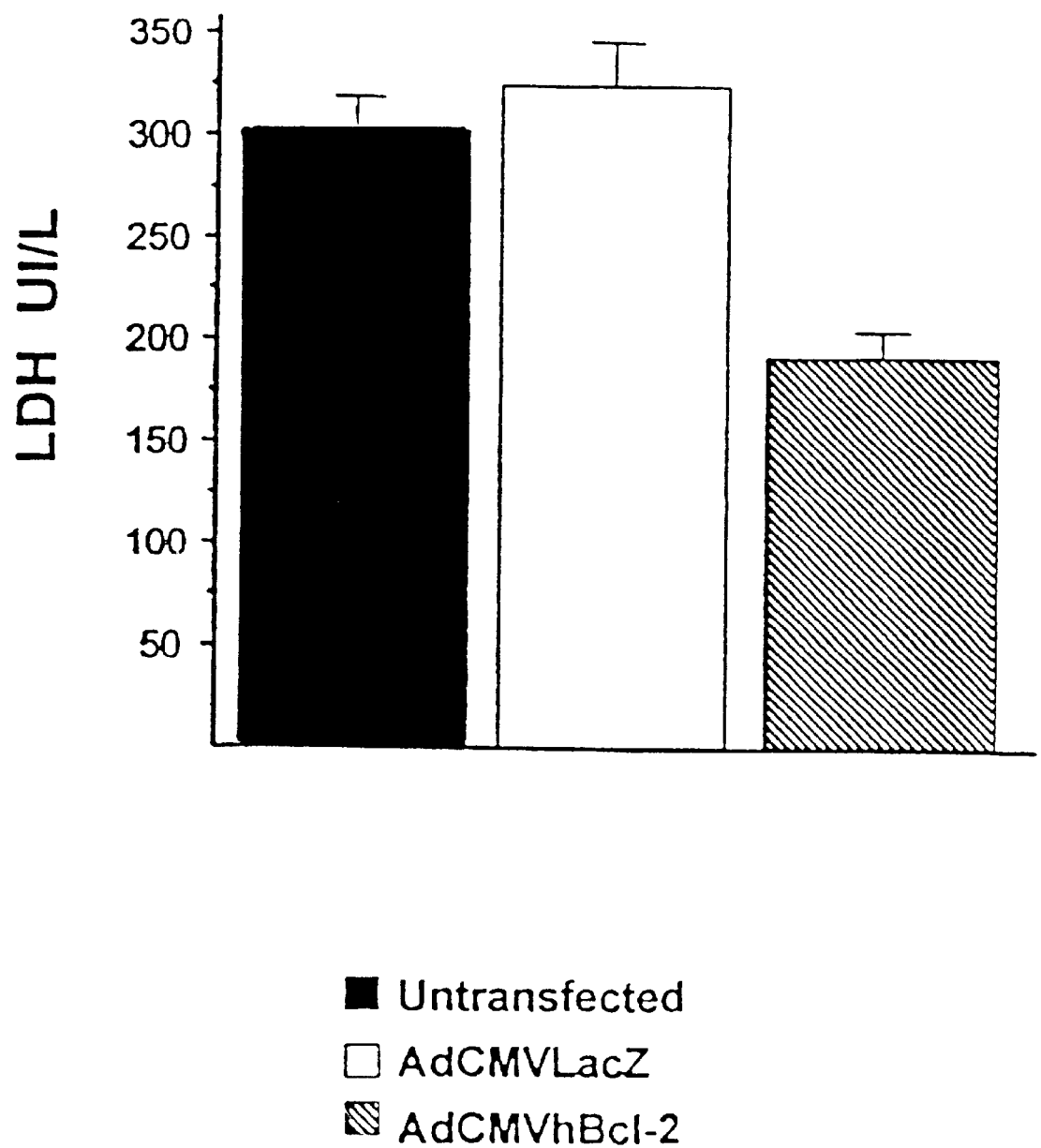
FIG. 11 shows cytoprotection of AdCMVhBcl-2 on liver grafts after rewarming at the end of the preservation time. Grafts harvested from untreated animals and animals injected with an adenovirus vector encoding an irrelevant gene released a significant higher lactate dehydrogenase compared with animals treated with AdCMVhBcl-2 ($1\times10^9$ pfu, $P<0.05$). Results are expressed as a mean±SEM.

From previous experiments, it was known that intravenous administration of adenoviral vectors, $1 \times 10^9$ pfu trans- Activity of Hepatocellular Enzymes After Graft Rewarming Hepatocellular damage and associated enzyme release occurs predominantly during the period of rewarming and warm ischemia (Ikeda, et al., 1992). AST activities in the preservation solution after 60 minutes of rewarming at-room temperature are demonstrated in FIG. 10. A significant release of aspartate amino transferase was observed in control animals and in animals transfected with an irrelevant gene. Significant reduction in aspartate amino transferase activity was observed in liver grafts expressing hBcl-2. Similar results were observed in ALT (data not shown) and LDH (FIG. 11). These results demonstrate a significant cytoprotective effect in livers transfected with hBcl-2 gene after rewarming.

Morphologic Assessment of the Grafts

Figure 12:
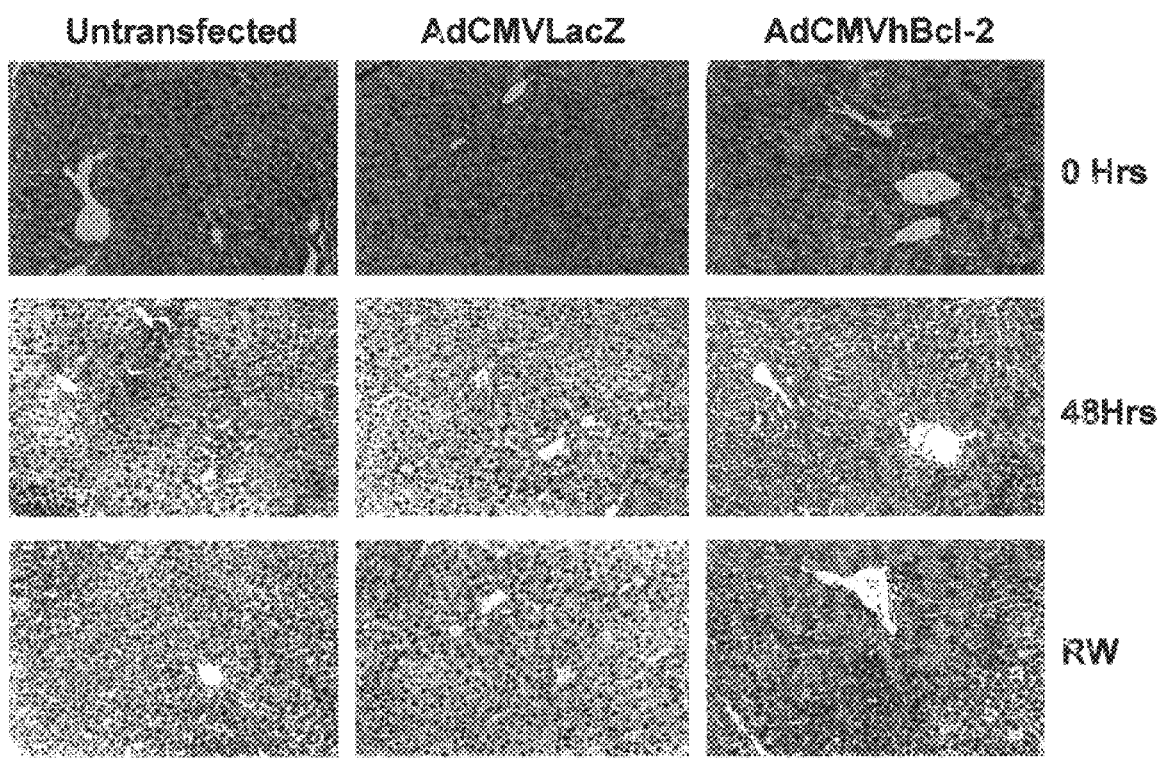
FIG. 12 shows histopathological analysis of liver grafts after the organ harvest (0 hours), at the end of the preservation time in UW solution at 4° C. (48 hours), and 60 minutes after "rewarming" (RW) at room temperature. Sections were evaluated at 40× magnification.

Histopathological features of liver samples during the preservation time and after rewarming are demonstrated in FIG. 12. No significant differences were observed between the three experimental groups after 24 hours of preservation. More cells with morphological characteristics of apoptosis (shrunken cells and single rounded cells or fragments with aggregation of the chromatin into uniform dense masses under the nuclear membrane) were identified in untransfected and livers transfected with AdCMVLacZ at 48 hours.

Figure 13:
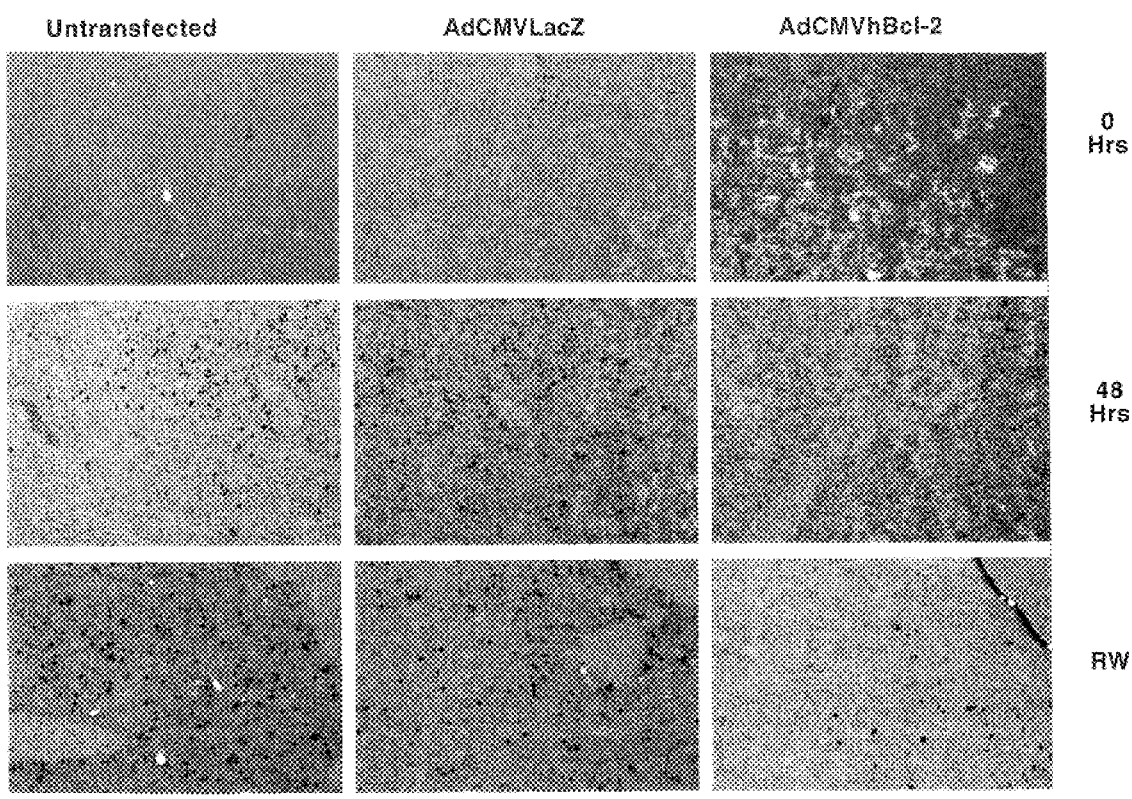
FIG. 13 shows apoptosis in liver grafts during the preservation time and after rewarming. Liver grafts from untreated and transfected with AdCMVLacZ presented higher number of positive apoptotic-stained cells than grafts genetically modified with AdCMVhBcl-2. Sections were evaluated at 80× magnification

Less apoptotic cells were observed in grafts cytoprotected with AdCMVhBcl-2. The difference was more evident after rewarming. Necrotic areas were also more prominent in control and AdCMVLacZ grafts compared with AdCMVhBcl-2 treated livers at the end of the preservation time (48 hours) and after rewarming (FIG. 13). In accordance with previous observations related to inflammatory response against the adenoviral vectors (Gao, et al., 1996; Wang, et al., 1997; Joose, et al., 1996), a neutrophilic infiltrate after the AdCMVLacZ administration was observed (FIG. 13). No significant infiltrates or inflammatory reaction was observed in livers transfected with AdCMVhBcl-2 (FIG. 13).

Apoptosis In Liver Grafts During the Preservation Time and After Rewarming

Detection of hepatocellular DNA fragmentation at the end of the preservation time (48 hours) and after rewarming is demonstrated in FIG. 13. The number of apoptotic cells scored semiquantitatively is demonstrated in Table 3. The extent of apoptosis is more evident in control and AdCVM-LacZ transfected livers compared to grafts expressing hBcl-2.

TABLE 3

Number of Apoptic Cells during Preservation Time and after Rewarming[a]

| Time | Control | AdCMVLacZ 1 × 10$^9$ pfu | AdCMVhBcl-2 1 × 10$^9$ pfu |
| --- | --- | --- | --- |
| 0 hr | 3.3 ± 7[b] | 22.9 ± 3[c] | 4.1 ± 3[b] |
| 48 hr | 99.6 ± 25[b] | 128.4 ± 20[b] | 15.2 ± 10[c] |
| Rewarming | 198.8 ± 33[b] | 256 ± 28[b] | 56.6 ± 17[c] |

EXAMPLE 24

Figure 14A:
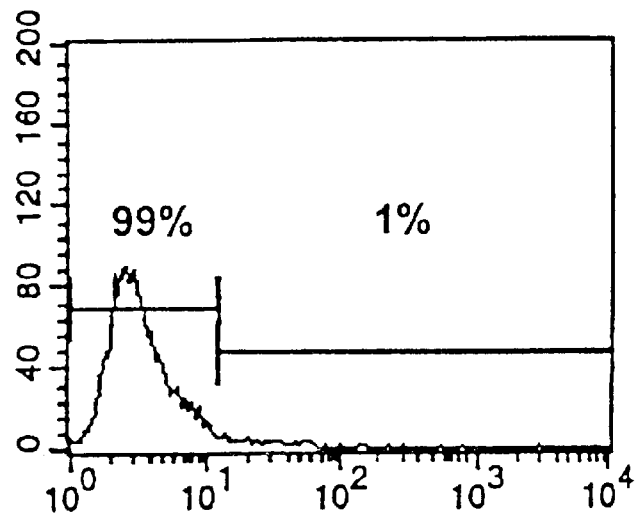
FIG. 14 shows transfection efficiency of adenoviral vectors into HUVEC's in vitro. 100% confluent HUVEC's were untransfected (FIG. 14A), transfected with 100 pfu/cell AdCMVLacZ (FIG. 14B), or with 500 pfu/cell AdCMV-LacZ (FIG. 14C). LacZ expression was obtained by FACS-Gal.
Figure 14B:
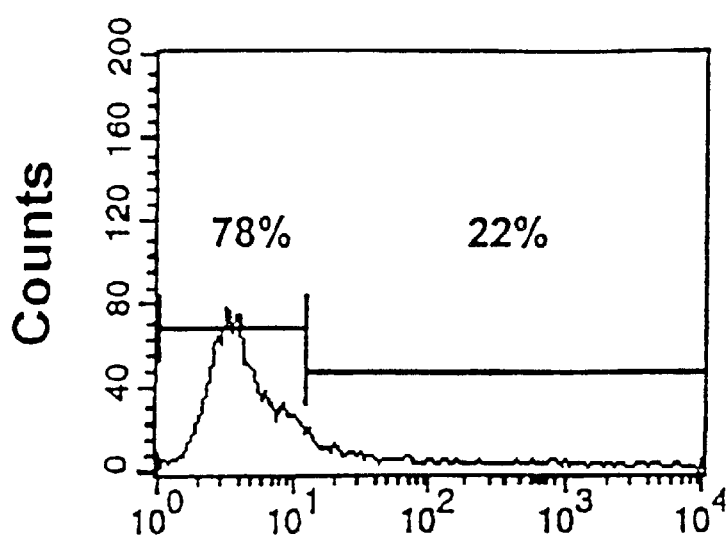
Figure 14C:
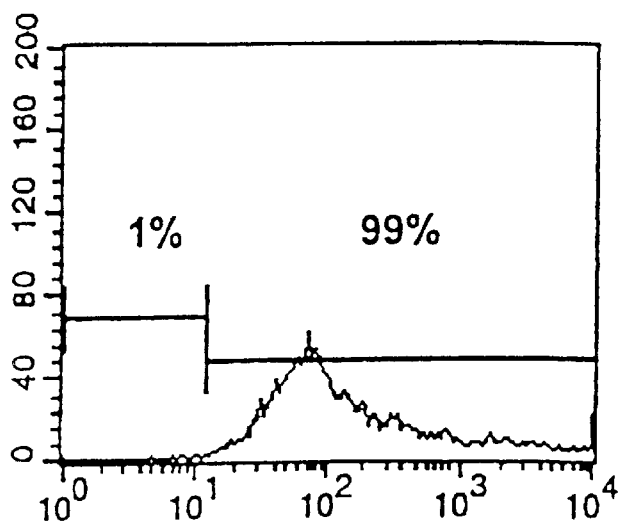

Cytoprotection Induced By Genetic Modification of Human Endothelial Cells (EC) During Preservation Time With an Adenoidal Vector Encoding the Anti-apoptotic Human Bcl-2 Gene Optimal Concentration of Adenovirus For Endothelial Cell Transfection The transfection efficiency on HUVEC's exposed a different plaque forming units (pfu) per cell of AdCMVLacZ is shown in FIG. 14. Less than 1% of control nontransfected cells were positive for X-gal staining, the transfection efficacy was 22% at 100 pfu/cell, and 99% at 500 pfu/cell. These results demonstrate that adenoviral vectors are highly efficient for gene transfer to endothelial cells in culture.

Expression of Human Bcl-2 Protein in HUVEC's

Figure 15:
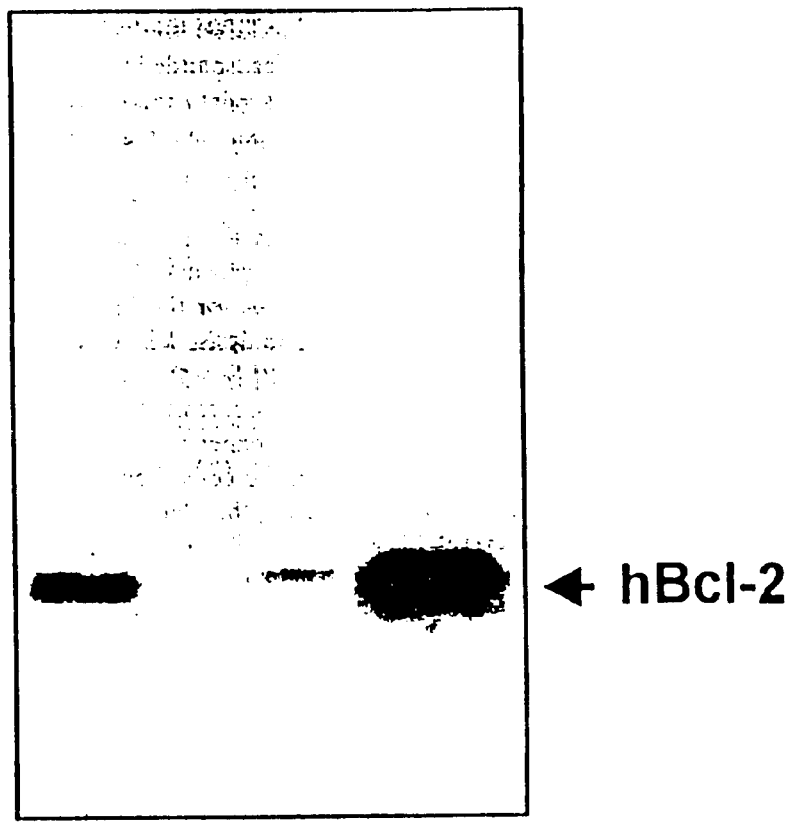
FIG. 15 shows immunoblot analysis of human Bcl-2 protein expression in HUVEC's. Lane 1: positive control; lane 2: non-transfected HUVEC's; lane 3: HUVEC's transfected with AdCMVLacZ 500 pfu/cell; lane 4: HUVEC's transfected with AdCMVhBcl-2 500 pfu/cell.

The expression of the human Bcl-2 protein was confirmed in HUVEC's (FIG. 15). Non-transfected HUVEC's were negative for hBcl–2 expression.

Cytoprotection of HUVEC's Induced By Genetic Modification With AdCMVBcl-2

Figure 16:
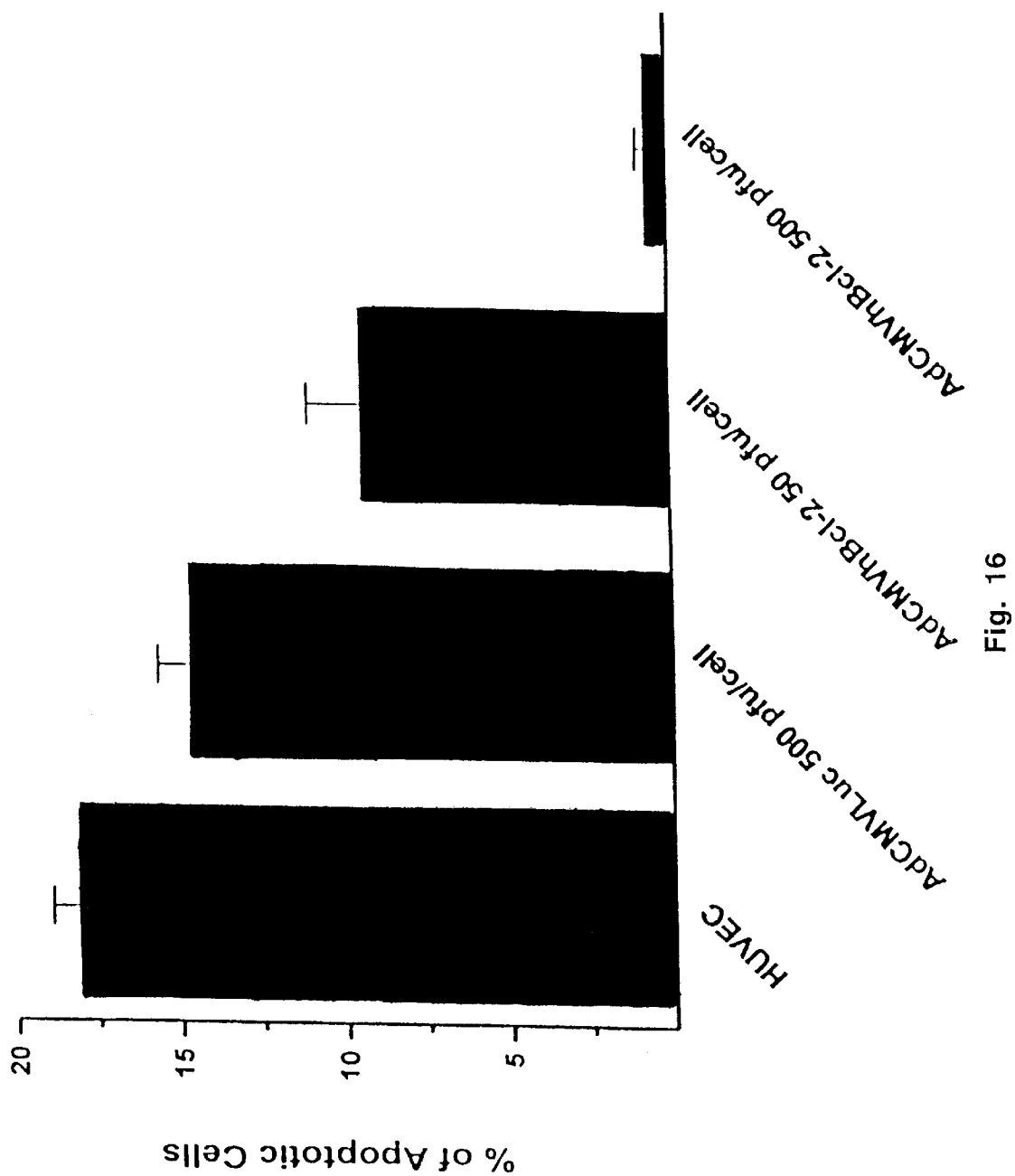
FIG. 16 shows cytoprotection of HUVEC's induced by genetic modification with AdCMVhBcl-2. Apoptosis analysis was performed using the ApoAlert Annexin V Fluos Stain Kit as described below. Results represent a mean percentage of apoptotic cells.

The injury induced during the cold preservation time in nearly confluent HUVEC's is shown in FIG. 16. After 48 hours of preservation time, the number of control non-transfected cells in apoptosis was 16±2%. Similar results were obtained in cell genetically modified with an irrelevant gene (AdCMVLacZ). A significant reduction in the percentage of apoptotic cells was observed in cells transfected with AdCMVhBcl-2, 9±3% and only 2±0.5% of HUVEC's were in apoptosis after 48 hours at 50 pfu/cell and 500 pfu/cell, respectively.

EXAMPLE 25

Figure 17:
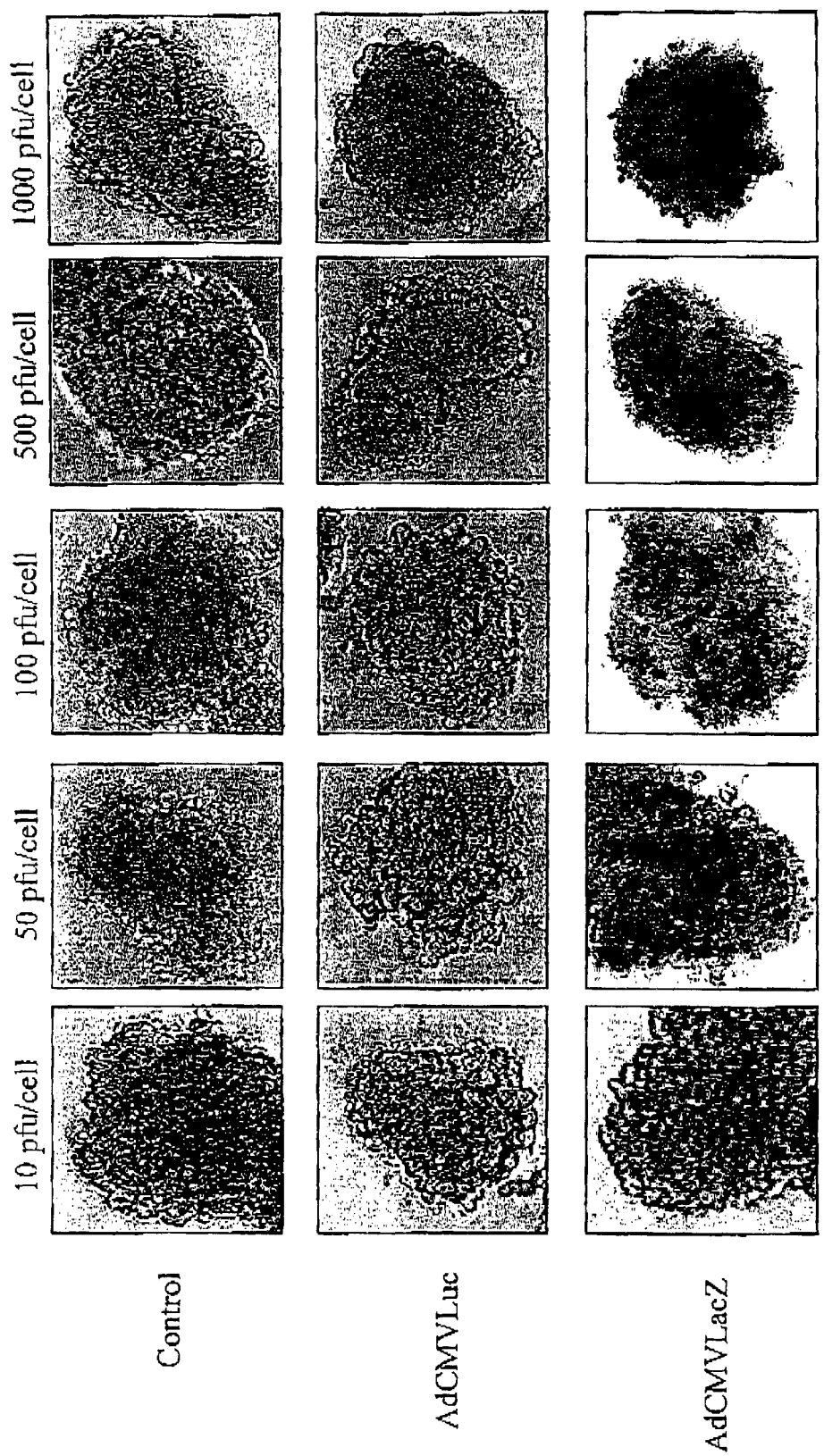
FIG. 17 shows efficient gene transfer to neonatal porcine islets in vitro demonstrated by β-galactosidase histochemical staining. Gene transfer was performed with adenoviral vectors encoding luciferase (AdCMVLuc) or β-galactosidase (AdCMVLacZ) at various (10, 50, 100, 500 and 1000) pfu/cell.

Adenovirus-Mediated Gene Transfer of the Human Anti-Apostolic Bcl-2 Gene Induces Cytoprotection of Neonatal Porcine Islets During Culture Time and Early After Transplantation Optimal Concentration of Adenoidal Vectors For Gene Transfer Into Neonatal Porcine Pancreatic Islets Gene transfer into neonatal pig islets has not been previously reported. Transfection efficiency of adenoviral vectors on neonatal porcine islets, as assessed by the expression of the LacZ marker gene, is shown in FIG. 17. The percentage of transfected cells increased in a dose-dependent relationship to the viral dose (MOI). Strong β-galactosidase activity was present in the periphery and center of the islet. Control islets and islets transfected with Luciferase did not demonstrate any X-gal staining (FIG. 17). At 250–500 MOI, more than 95% of the cells in the islet were transfected with adenoviral vectors. Higher transfection efficiency with lower MOI were observed in neonatal porcine islets compared with murine and nonhuman primate pancreatic islets. These results demonstrate the feasibility of gene transfer into neonatal pancreatic islets with recombinant adenoviral vectors.

Figure 18:
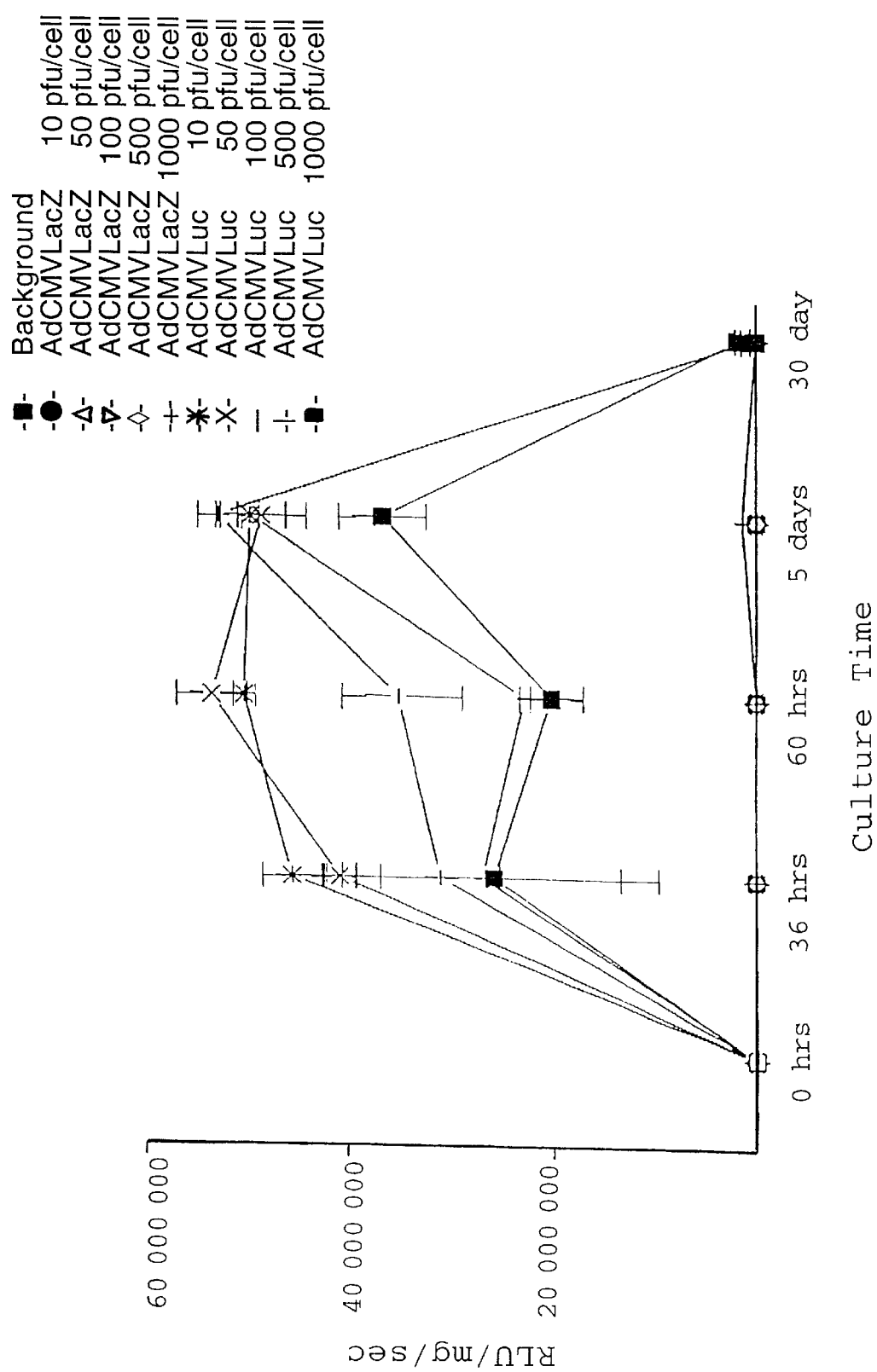
FIG. 18 shows transgene expression in neonatal pancreatic islets in culture. Gene transfer was performed with adenoviral vectors encoding luciferase (AdCMVLuc) or β-galactosidase (AdCMVLacZ) at various (10, 50, 100, 500 and 1000) pfu/cell. Results are expressed as mean±standard deviations.

Expression of the transgene during the culture time, analyzed as luciferase expression, is shown on FIG. 18. High levels of expression were observed in islets transfected with low viral concentration (10 pfu/cell) at 36, 60 and 120 hours. Gene transfer with 1000 pfu/cell produced only 50% of the transgene expression compared with 10 or 50 pfu/cell, probably related to islet toxicity. Murine pancreatic islets transfected with adenoviral vectors at 1000 pfu/cell induced a deleterious effect on the islet cell function, with increased in apoptosis during the first days after gene transfer. Low levels of transgene expression were observed in neonatal islets after 30 days in culture independently of the viral dose used for the gene transfer. These results demonstrated that porcine pancreatic islets can be genetically modified ex vivo, during the culture time, with lower viral dose compared with pancreatic islets from other species and the transgene expression is limited, ex vivo to less than 30 days.

Expression of Human Bcl-2 Protein In Neonatal Porcine Islets

Figure 19:
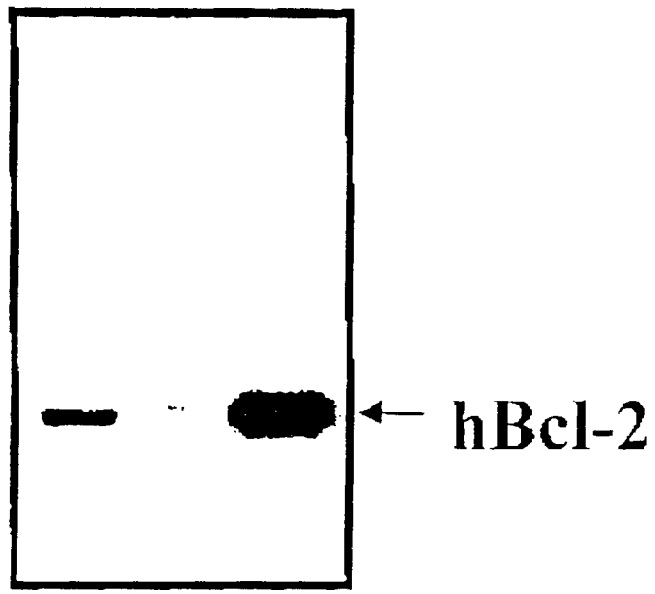
FIG. 19 shows immunoblot analysis of human Bcl-2 protein expression in neonatal porcine islets.

The expression of the human Bcl-2 protein was confirmed in neonatal porcine islets. (FIG. 19). Non-transfected neonatal porcine islets or islets transfected with an irrelevant gene were negative for hBcl-2 expression.

Figure 20A:
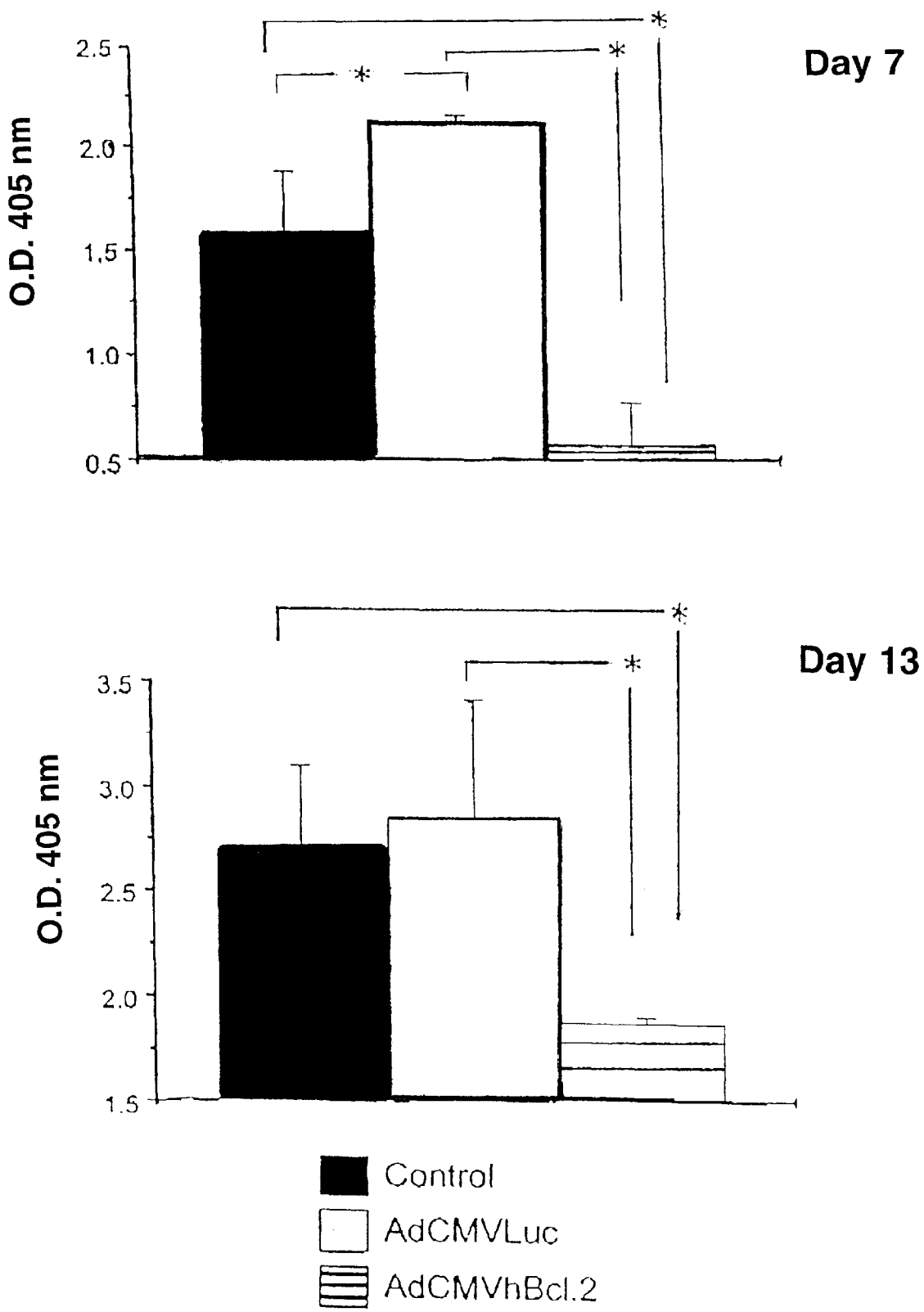
FIGS. 20A and 20B show reduced DNA fragmentation in neonatal porcine islets cytoprotected with Bcl-2. DNA fragmentation was determined using a sandwich ELISA on days 7, 13 and 30 of the culture. Results are expressed as mean±standard deviations. *p<0.05.
Figure 20B:
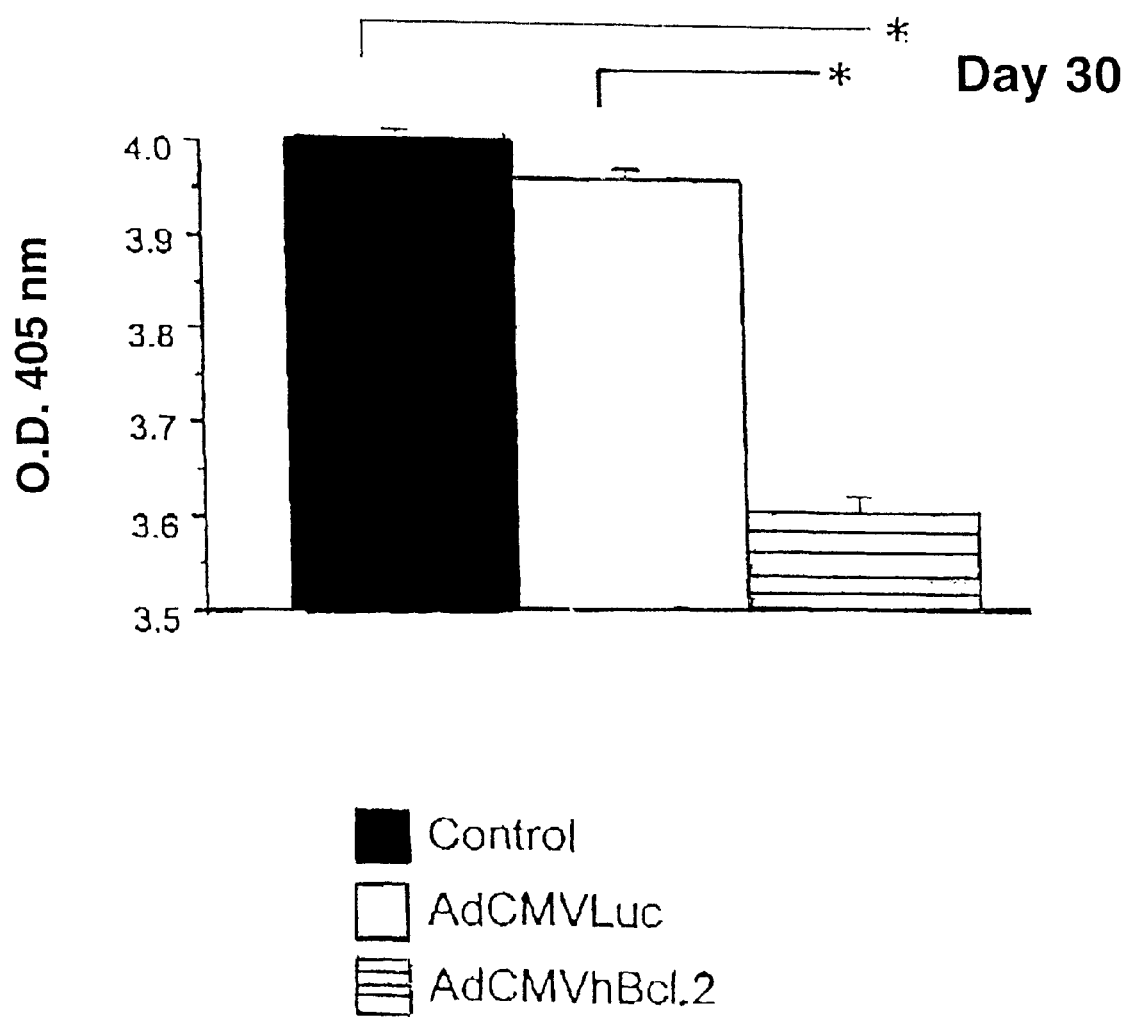

Cytoprotection of neonatal porcine islets during the culture time by genetic modification with AdCMVBcl-2: DNA fragmentation is the biochemical marker of apoptosis. As previously reported in human islets, apoptosis is a frequent event during standard culture time before transplantation. Islet cell DNA fragmentation assessed by ELISA assay during the culture time is shown on FIGS. 20A and 20B. Islets transfected with AdCMVhBcl-2 at a dose of 100 pfu/cell showed approximately 65% reduction in the DNA fragmentation after 7 days in culture compared with control untransfected islets. Higher DNA fragmentation was observed in cells transfected with an adenoviral vector encoding an irrelevant gene (AdCMVLuc) compared with untransfected islets, demonstrating some degree of cytotoxic effect of adenoviral vectors in neonatal porcine islets. Significant reduction in DNA fragmentation was also observed in islet transfected with hBcl-2 at 13 and 30 days of the culture time (FIGS. 20A and 20B). These results demonstrate the cytoprotective properties of the anti-apoptotic hBcl-2 gene in neonatal porcine islets.

Islet Transplant Survival

Figure 21:
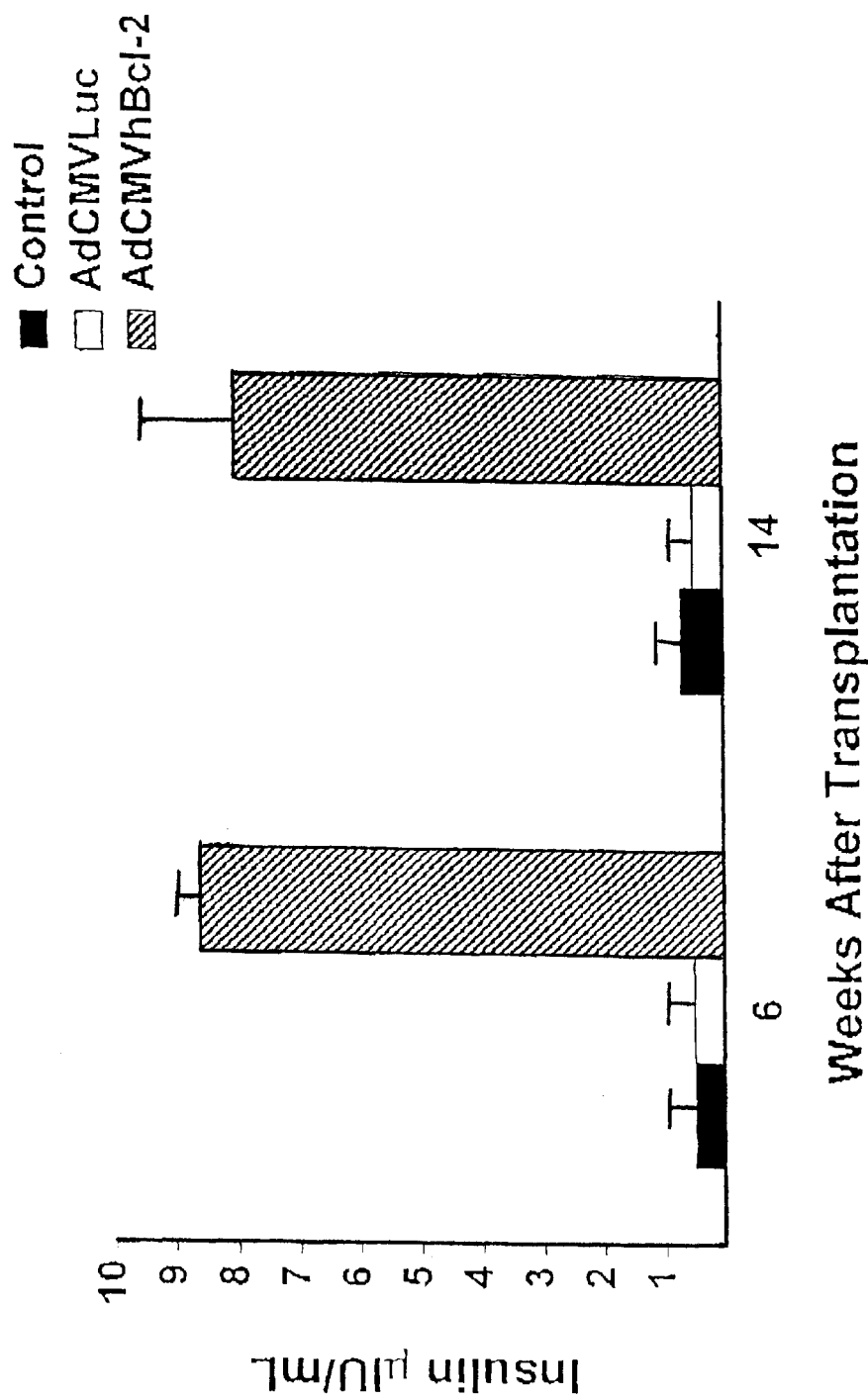
FIG. 21 shows insulin release after transplantation of genetically modified neonatal porcine islets. After 7 days in culture, 500–700 untransfected, AdCMVLuc and AdCMVhBcl-2 transfected islets were transplanted intraperitoneally in SCID mice. Stimulated plasma insulin levels (glucose 0.5 mg/kg/intraperitoneally/5–8 minutes before blood sample) were obtained 6 and 14 weeks after the transplant.

Islet transplantation to immunocompromised SCID mice was used to demonstrate the in vivo function of control and transfected (AdCMVLuc and AdCMVBcl-2) neonatal islets. Insulin release in vivo 6 and 14 weeks after transplantation was only demonstrated in animals that received neonatal pig islets cytoprotected with hBcl-2 (FIG. 21). Therefore, overexpression of hBcl-2 after islet isolation and early after transplantation induces islet cytoprotection in vivo during the most critical survival time. Genetic modification of neonatal porcine islets with AdCMVhBcl-2 do not seems to interfere with insulin release as has been demonstrated in experiments of gene transfer using recombinant adenoviral vectors.

EXAMPLE 26

Protection of Adenoidal Vector Transduced Cells and Prolongation of Transgene Expression With an Adenoidal Vector Encoding the Anti-apoptotic Bcl-2 Gene Bcl-2 Expression In Liver To test whether AdCMVhBcl-2 could mediate transfer of the Bcl-2 gene to the liver, adult female C57BL/6 mice were injected intravenously (I.V.) with AdCMVhBcl-2 plus AdCMVLuc, with a control vector AdCMVLacZ plus AdCMVLuc at $1 \times 10^9$ pfu per vector (total dose $2 \times 10^9$), or with phosphate buffered saline (PBS) alone. Immunohistochemical staining of the hBcl-2 protein demonstrated transduction of >90% of hepatocytes. At 48 hours post-injection, total RNA was extracted from the livers and subjected to RT-PCR. As shown in FIG. 2B, expression of the Bcl-2 gene could be detected in livers from mice injected with AdCMVhBcl-2, but not in livers from animals treated with the control vector or PBS. Thus, Bcl-2 expression in the liver can be accomplished in vivo after systemic administration of a recombinant adenovirus encoding Bcl-2.

Figure 22:
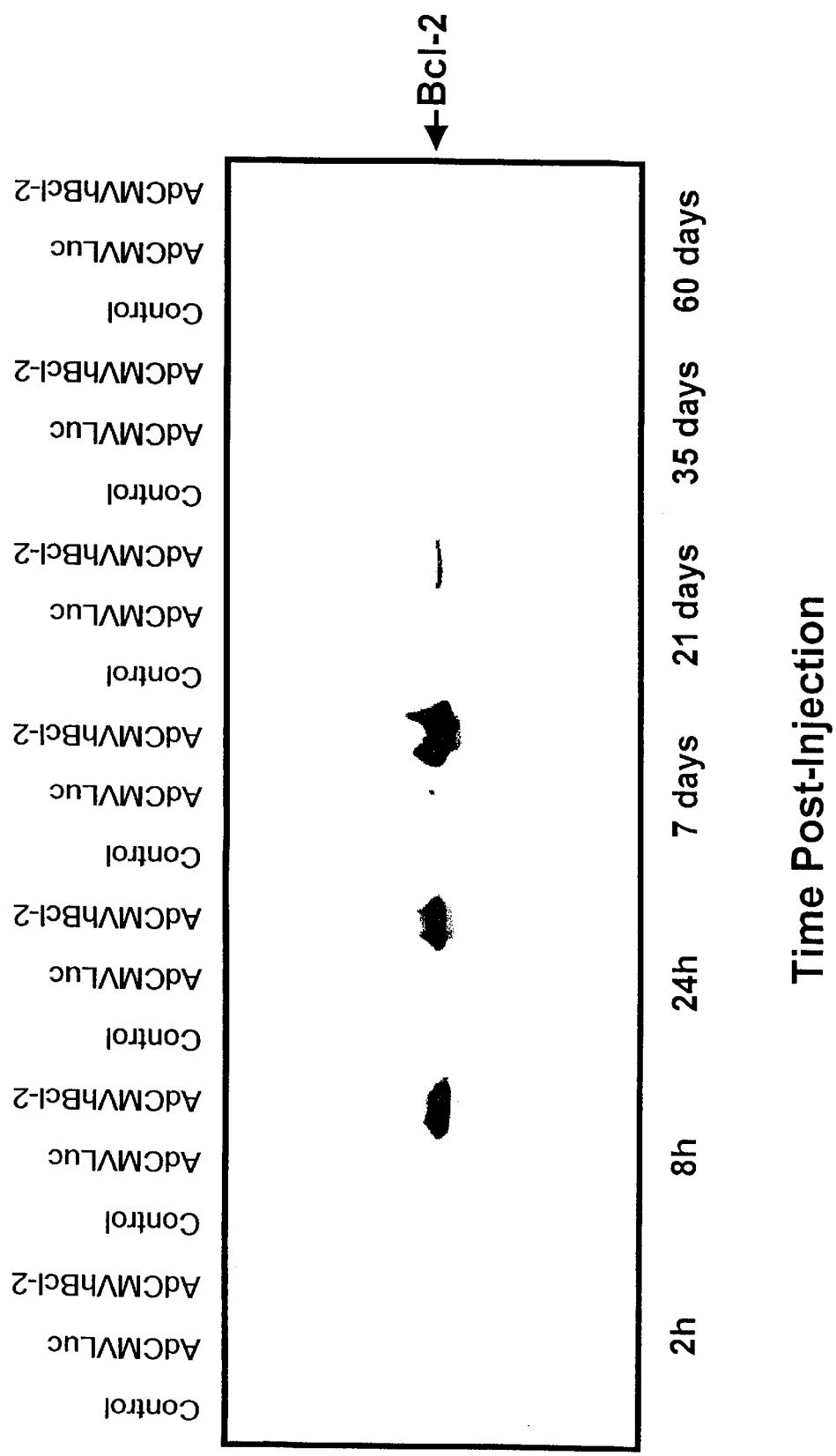
FIG. 22 shows immunoblot analysis of human Bcl-2 protein expression. Adult C57Bl/6 mice were injected intravenously with either AdCMVhBcl-2 plus AdCMVLuc, or AdCMVLacZ plus AdCMVLuc at $1\times10^9$ pfu per vector (total dose $2\times10^9$). Control animals did not receive viral injection. At various time points post-injection, total protein was extracted from frozen livers. Fifteen micrograms of total protein were size-fractionated by 12% SDS-PAGE. The membrane was developed with Western blot chemoluminescence reagent.

In Vivo Liver Expression of the hBcl-2 Encoded By AdCMVhBcl-2 at Different Time Points Post-injection An immunoblot analysis of human Bcl-2 protein was employed. Fifteen micrograms of total protein from cellular lysate prepared as described elsewhere (Promega Luciferase Assay System) were size-fractionated by 12% sodium dodecyl sulfate-polyacrylamide (SDS) gel electrophoresis and electroblotted onto a nitrocellulose membrane. The human Bcl-2 protein was detected using the monoclonal antibody mouse anti-human Bcl-2 (Oncogene Research Products, Cambridge, Mass.) at a 1:3,000 dilution, followed by the addition of goat anti-mouse HRP antibody. The membrane was developed with Western blot chemoluminescence reagent (DuPONT NEN, Boston, Md.). As control for equal loading of protein c-myc was also detected. Reference Coomassie-stained gels were also run. The molecular weight of the Bcl-2 is 25 kDa. As showed in FIG. 22, Bcl-2 protein expression can be detected by Western Blot at 8 hours post-injection with a maximum expression by 7 days, and was almost undetectable by day 21. No detection of human Bcl-2 was demonstrated in the control group or in animals treated with AdCMVLuc.

Hepatotoxic Effect of the Adenovirus Vector

Figure 23:
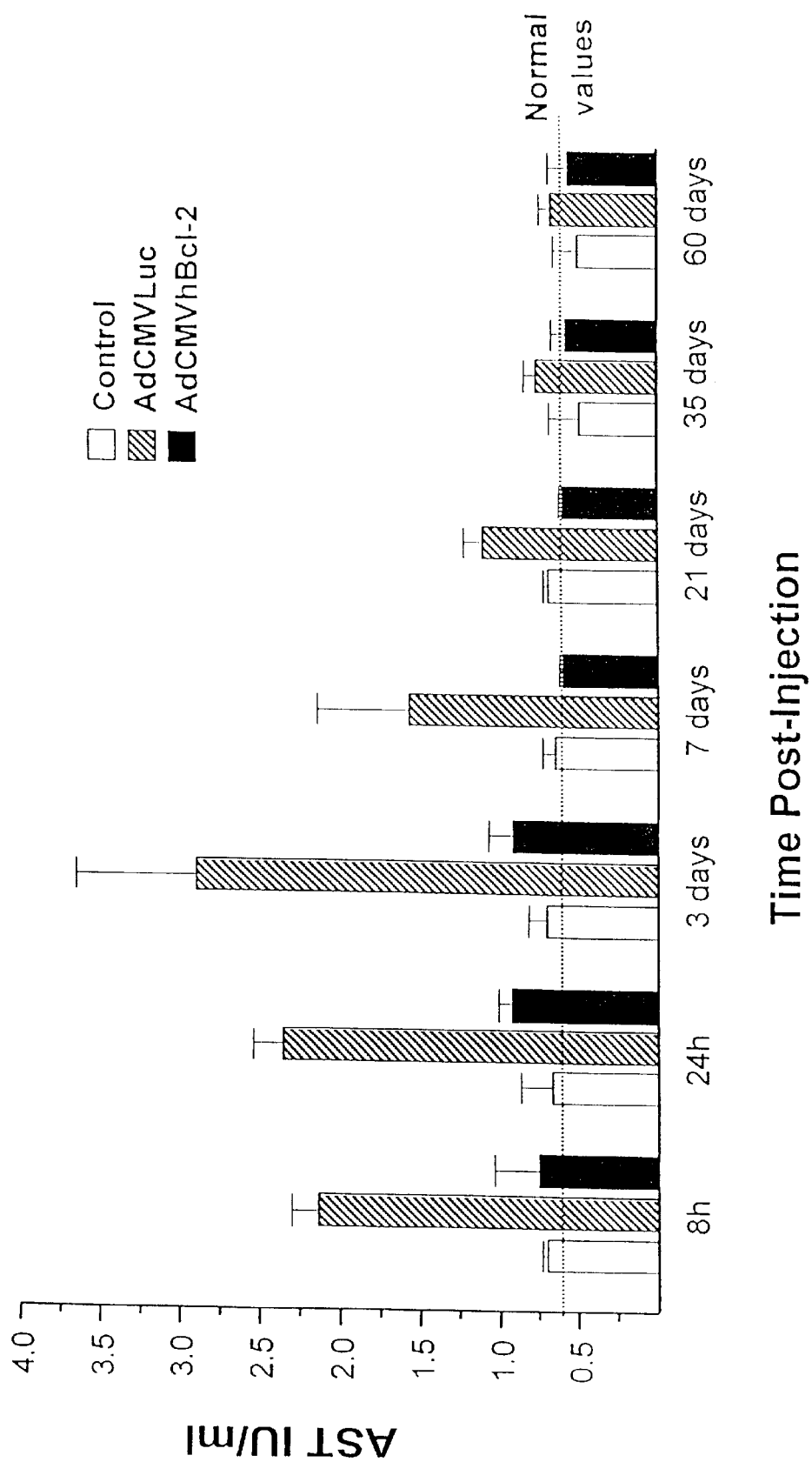
FIG. 23 shows aspartate amino transferase levels after adenovirus-mediated gene transfer. Adult female C57Bl/6 mice were injected I.V. with either AdCMVhBcl-2 plus AdCMVLuc, or AdCMVLacZ plus AdCMVLuc at $1\times10^9$ pfu per vector (total dose $2\times 10^9$). Serum AST levels were measured at various time points post-injection. Results are expressed as a mean±SEM of eight animals. Serum aspartate amino transferase levels obtained from normal C57Bl/6 mice were 0.58±0.08 UI/L. Significant difference was observed between AdCMVhBcl-2 group compared with controls or AdCMVLacZ injected animals (p=<0.01, Student's t test).

Liver function test was analyzed after the in vivo gene delivery. Blood samples for aspartate amino transferase determinations were obtained at different time points post adenoviral administration, AST was analyzed using a serum analyzer (Amos Seralyzer, Miles Inc, Diagnostics Division, Elkhart, Ind., USA). Animals from the control group injected with PBS showed normal serum aspartate amino transferase levels in all time points (FIG. 23). Animals treated with AdCMVhBcl-2 plus AdCMVLuc showed a similar profile in aspartate amino transferase levels. In contrast, animals infected with AdCMVLuc plus AdCMVLacZ showed a significant increase in AST levels beginning at 8 hrs with a pick at 3 days, and returned to baseline levels at day 35 post-injection (FIG. 23). Similar results were observed with alanine amino transferase and lactate dehydrogenase determinations. These results demonstrate that adenovirus-mediated gene transfer of the anti-apoptotic Bcl-2 gene induces cytoprotection of the adenovirus vector transduced cells.

Hepatocyte Injury By Histological Analysis

Figure 24:
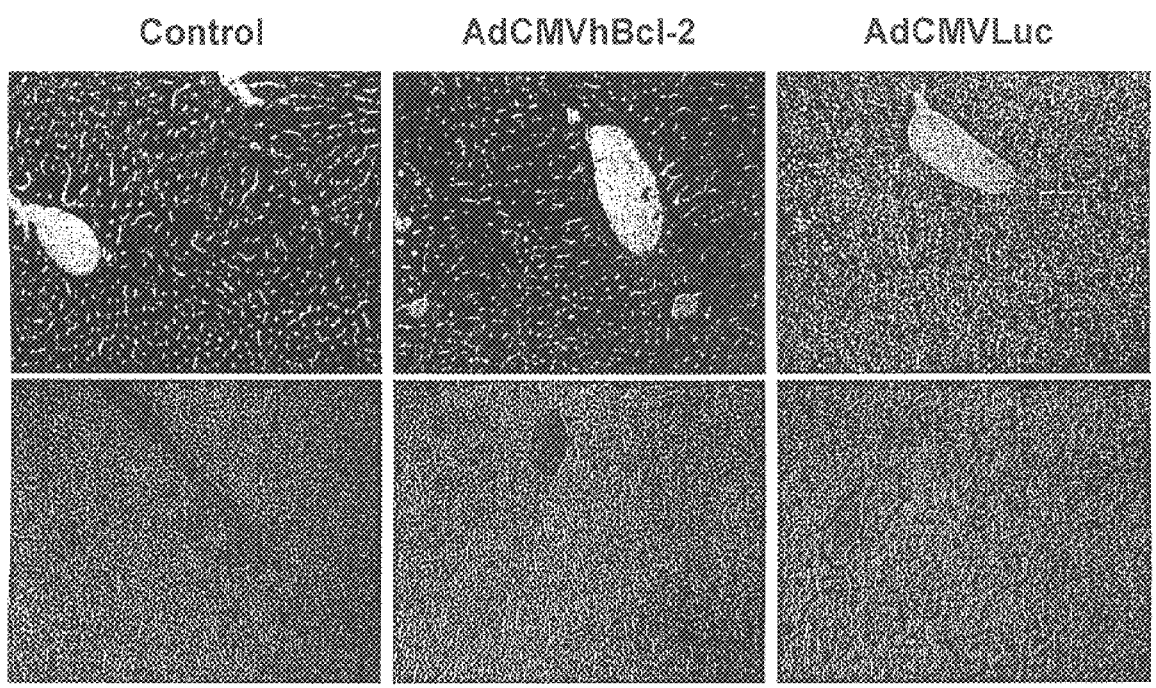
FIG. 24 shows histological and apoptosis analysis of the liver after human Bcl-2 expression in the liver. Adult female C57Bl/6 mice were injected I.V. with either AdCMVhBcl-2 plus AdCMVLuc, or AdCMVLacZ plus AdCMVLuc at $1\times10^9$ pfu per vector (total dose $2\times10^9$). Liver were harvested 3 days post-injection and sections were prepared for histological analysis staining with haematoxylin and eosin. Apoptosis was detected with in situ histochemical assay for DNA fragmentation (Klenow-FragEL). Magnification 25×.

Liver biopsies for histological assessment were obtained at different time points after the systemic administration of the adenovirus vectors. Liver specimens from the median lobe were fixed in 10% formalin and embedded in paraffin. Six-micrometer hematoxylin and eosin (H&E)-stained sections were evaluated at 100× magnification by a point-counting method for severity of hepatic injury using an ordinal scale as previously described: grade 0: minimal or no evidence of injury; grade 1: mild injury consisting in cytoplasm vacuolation and focal nuclear pyknosis; grade 2: moderate to severe injury with extensive nuclear pyknosis, cytoplasmic hypereosinophilia, and loss of intercellular borders; and grade 3: severe necrosis with disintegration of hepatic cords, hemorrhage and neutrophils infiltration (Camargo, et al., 1997). The results demonstrate that control animals injected with PBS did not shown any evidence of hepatic injury (grade 0, FIG. 24). Consistent with the transaminases levels (FIG. 23), the group injected with AdCMVLuc plus AdCMVLacZ shown moderate to severe injury by day 3 after the systemic administration of the adenoviral vector (Grade 2–3) with nuclear pyknositosis, cytoplasmic hypereosinophilia, and loss of intercellular borders. Areas of necrosis with disintegration of hepatic cords and neutrophils infiltration were also evident (FIG. 24). The hepatotoxic effect of the adenovirus vector was less evident by day 7, and resolved by day 35. Animals injected with AdCMVhBcl-2 plus AdCMVLuc showed minimal evidence of injury (grade 0–1) in all the experimental time points (FIG. 24). These results suggest that Bcl-2 might protect the host cell against the cytotoxic effects of the adenovirus vector and decrease the inflammatory response secondary to the viral infection.

Apoptosis Detection

A commercial in situ histochemical assay (Klenow-FragEL, Oncogene Research Products, Cambridge, Mass.) was used to detect the DNA fragmentation characteristic of apoptosis in the liver cells, using the same procedure as described in Example 15. The results showed that apoptotic cells were more evident in samples from animals injected with AdCMVLuc plus AdCMVLacZ (FIG. 24). In contrast, significant lesser number of apoptotic cells were present in the animals co-injected with the AdCMVhBcl-2 plus AdCMVLuc (FIG. 24). Thus, these results demonstrate that apoptosis plays a critical role in the clearance of the adenovirus vector at early time post injection, and the ability of hBcl-2 to block the apoptosis process induced by the adenovirus vectors.

Potential Biologic Effect of hBcl-2 In Transgene Expression

Figure 25:
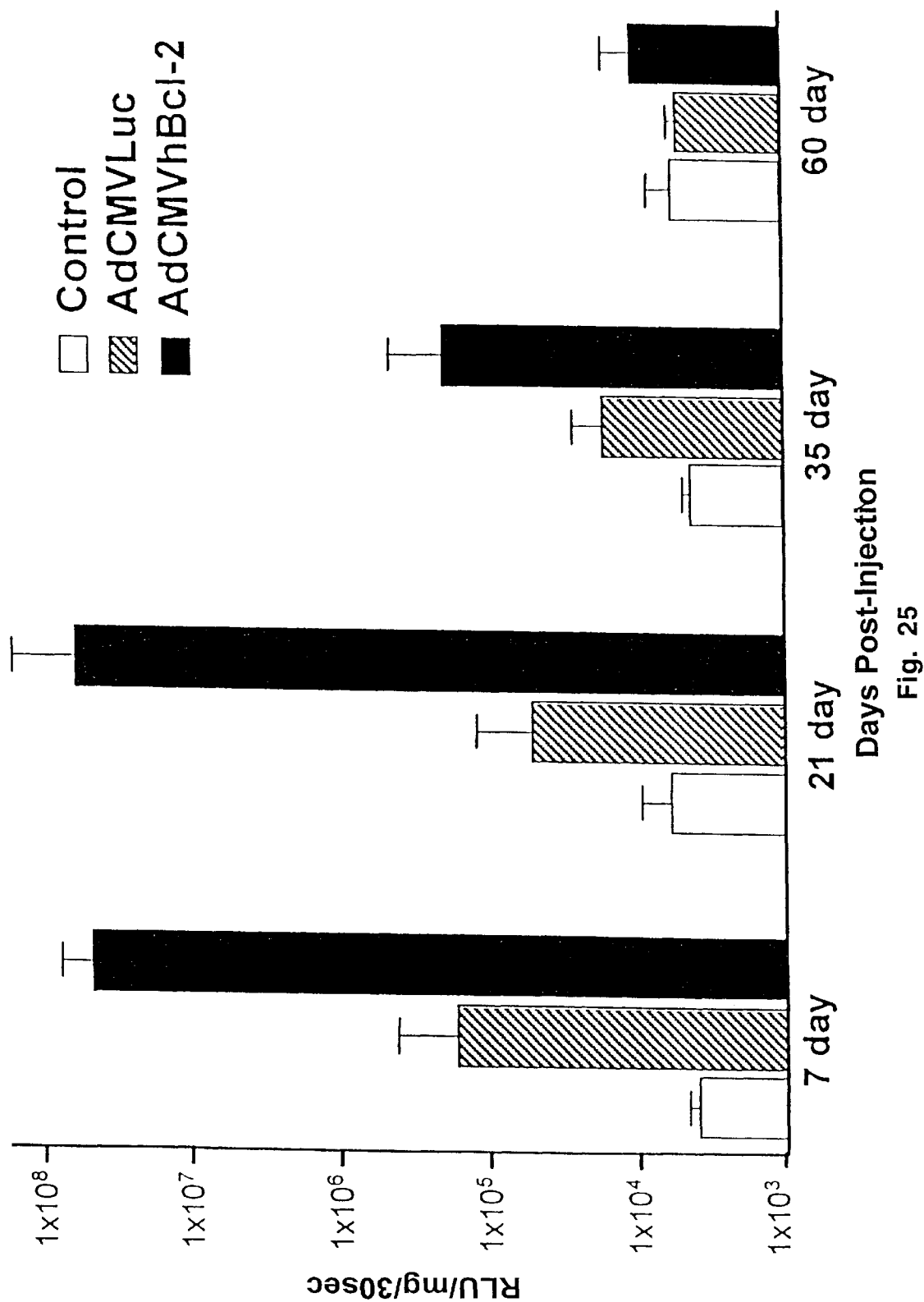
FIG. 25 shows effect of ectopic expression of human Bcl-2 on transgene expression in murine hepatocytes. Adult C57Bl/6 mice were injected intravenously with either AdCMVhBcl-2 plus AdCMVLuc, or AdCMVLacZ plus AdCMVLuc at $1\times10^9$ pfu per vector (total dose $2\times10^9$). Control animals did not receive viral injection. At various time points post-injection, luciferase activity was determinated in harvested frozen livers. Each histogram represents the mean±SEM of eight animals.

Adult female C57Bl/6 mice were injected via the tail vein with adenoviral vectors. Animals were challenged with both AdCMVLacZ plus AdCMVLuc, or AdCMVhBcl-2 plus AdCMVLuc, at $1 \times 10^9$ pfu per vector per animal. Analysis of luciferase reporter gene expression was assayed as described by the manufacturer (Promega Luciferase Assay System). Briefly, lysates cells were washed with PBS and then 400 μl of Promega 1×cell culture lysis reagent was added to the cells. Samples were then incubated on ice for 1 hour, after which lysates were collected and spun down at 14,000 rpm for 5 minutes. Next, 20 μl of supernatant was added to 100 μl of Promega Luciferase Substrate and analysis of emitted light. Lumat LB 9510 luminometer using the parameters described by the manufacturer was used to analyze the light units. Results are expressed as reading of light unites (RLU)

per milligram of total protein per 30 seconds. As expected, all uninfected control groups demonstrated an absence of luciferase expression in harvested livers. In the group treated without hBcl-2 expression, an initial high level of gene expression was achieved by day 7 post-infection followed by progressive attenuation in a time-dependent manner such that by day 60 post-infection the magnitude of luciferase gene expression was at baseline (FIG. 25). This pattern of non-persistence of transgene expression is analogous to that described by other authors, and reflects, in part, the consequences of the host immune response to the vector-transduced cells (Lieber, et al., 1998; Perez, et al., 1998; Zhang, et al., 1998). However, in situ co-expression of hBcl-2 protein induced a different pattern of transgene expression compared to AdCMVLacZ plus AdCMVLuc treated animals (FIG. 25). In this regard, a two log increase of transgene expression by day 7 and 21, and 1 log increase in transgene expression by day 35 post-injection was noted. It was also noted that some degree of prolongation of transgene expression was achieved by day 35 post-transfection, however b y day 60 the magnitude of luciferase expression was nearly baseline. It appeared that, in this organ context, simple ectopic expression of hBcl-2 did confer the desired end of cytoprotection of the vector-infected cell, achieving enhancement and some degree of prolongation of transgene expression.

Discussion

The present invention demonstrates that an adenovirus vector carrying the anti-apoptotic human Bcl-2 gene could mediate cytoprotection of the liver against ischemia/reperfusion-injury in vivo. Furthermore, permanent survival was achieved following a lethal warm ischemia/reperfusion-injury. The beneficial effect of Bcl-2 on reperfusion injury seems to be related to its anti-apoptotic and anti-necrotic properties. Prevention or reduction of ischemia/reperfusion-injury with gene therapy could be an attractive therapeutic alternative in multiple clinical conditions such as liver surgery and organ transplantation and other conditions associated with I/R-Injury.

Also demonstrated in the present invention is that genetic modification of liver grafts with the anti-apoptotic human Bcl-2 gene before the organ procurement conferred cytoprotection during the preservation time and rewarming, therefore, gene therapy represents a potentially attractive. approach for improved organ preservation.

Preservation of solid organs in hypothermia is a basic requirement in transplantation. Endothelial cell damage has been demonstrated during organ preservation and after reperfusion. The present invention suggests that gene transfer to human endothelial cells with an adenovirus vector encoding the hBcl-2 gene induced a significant cytoprotection against apoptosis induced during cold preservation. Cytoprotection of endothelial cells might potentially increase the survival of allografts, xenografts, prevent the upregulation of proinflammatory genes after transplantation, and reduce transplant atherosclerosis.

The present invention additionally shows that gene transfer to neonatal pancreatic islets is feasible with low concentration of recombinant adenoviral vectors. Bcl-2 expression protects the neonatal pancreatic islets from apoptosis during the culture time and allows insulin secretion after transplantation. Therefore, targeting the apoptosis pathway with gene transfer of Bcl-2 is an attractive cytoprotective alternative on pancreatic islets during culture time and early after transplantation. Gene transfer of anti-apoptotic genes is a potential new therapeutic approach for successful islet transplantation.

Figure 26:
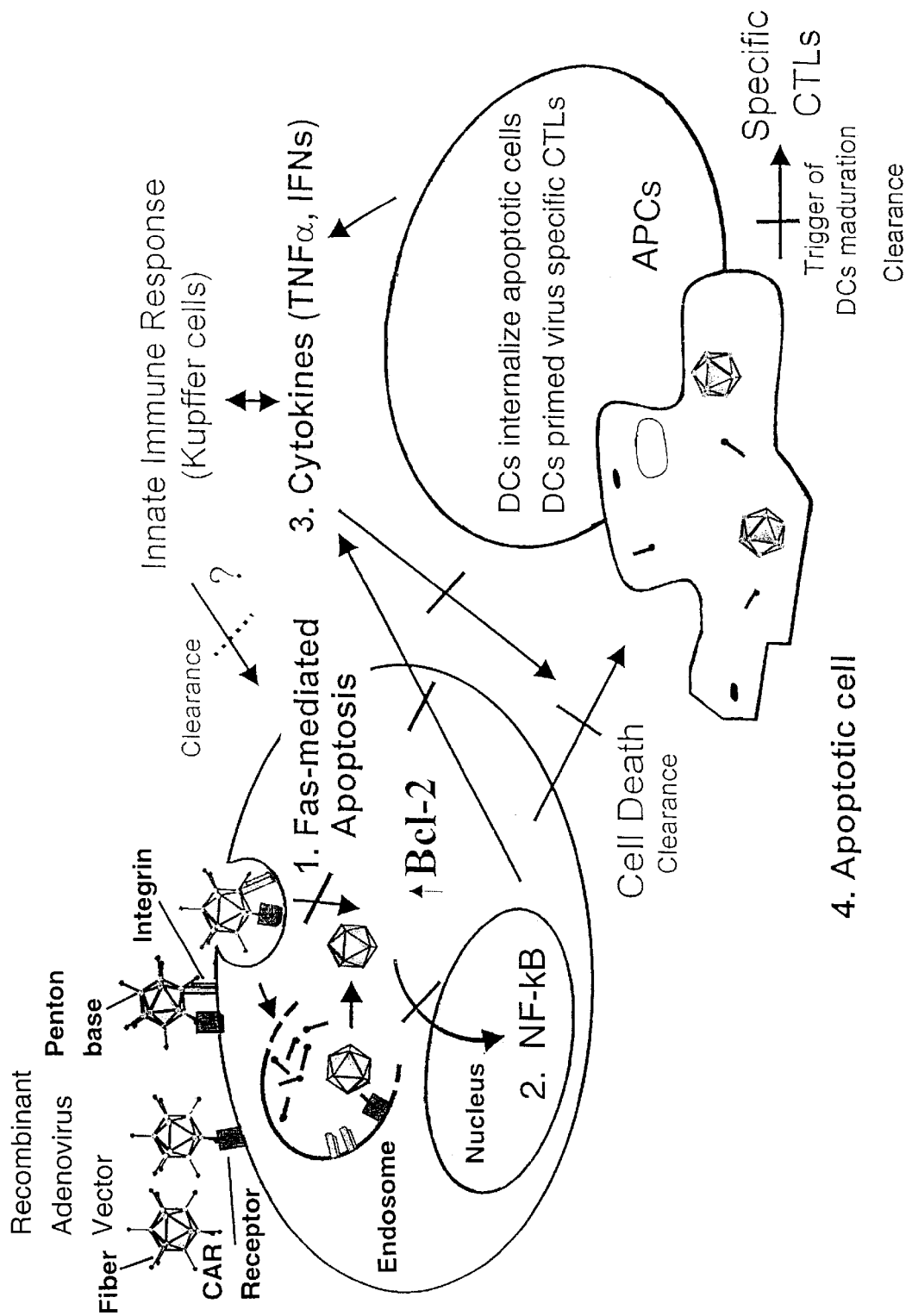
FIG. 26 shows proposed scheme of events in adenovirus-mediated enhancement of transgene expression by the anti-apoptotic Bcl-2 gene.

The co-expression of Bcl-2 mediated a significant reduction in apoptosis and necrosis following adenovirus mediated gene transfer, achieving an enhancement of transgene expression (up to 2 log). These results suggest that apoptosis plays an important role in the early clearance of the adenovirus infected cells. The proposed scheme of events in adenovirus-mediated enhancement of transgene expression by coexpression of the anti-apoptotic Bcl-2 gene are shown in FIG. 26. Transient expression of Bcl-2 at the time of adenovirus IV injection was sufficient to enhance and prolong transgene expression. It is anticipated that the simultaneous expression of Bcl-2 with a therapeutic gene might be effective in preventing the rapid elimination of hepatocytes transduced with an adenoviral vector. Strategies to prolong the expression of therapeutic genes delivered by adenovirus vector, even in the context of diseases in which transient effects may be sought, are essential requirements for achieving clinical utility.

The following references were cited herein.
1. Seemayer, T. A., et al. (1989) Lab. Invest. 60, 585–599.
2. Weinberg, R. A. (1996) Sci. Am. 275, 62–70.
3. Oncolink page "Molecular biology and XXX". URL: http://oncolink.upenn.edu/specialty/mol_bio/
4. Bilbao, G., et al. (1997) Exp. Opin. Ther. Patents 6, 1267–1284.
5. Sikora, K. (1993) Trends In Biotechnology 11, 197–201.
6. Dorudi, S., et al. (1993) Br. J. Surg. 80, 566–572.
7. Freeman, S. M., et al. (1993) Cancer Investigation 11, 676–688.
8. Vanchieri, C. (1993) J Natl. Cancer Inst. 85, 90–91.
9. Lemoine, N. R., et al. (1993) BMJ. 306, 665–666.
10. Gutierrez, A., et al. (1992) Lancet 339, 715–721.
11. Karp, J. E., et al. (1994) Cancer Res. 54, 653–665.
12. Hwu, P., et al. (1992) Ann.Oncol. 3, 198 1992.
13. Rosenberg, S. A. (1994) Prev. Med. 23, 624–626.
14. Rosenberg, S. A., et al. (1995) Ann. Surg. 218, (4):455–63;
15. Wilson, J. M. (1996) New England J. of Med. 334, 1185–1187.
16. Wilson, J. M., et al. (1994) Hum. Gene Ther. 5, 501–519.
17. Rosenfeld, M. A., et al. (1996) Chest. 109, 241–252.
18. Korst, R. J., et al. (1995) American J. of Respiratory & Critical Care Medicine 151, S75–87.
19. Coutelle, C. (1995) Biologicals. 23, 21–25.
20. Wagner, J. A., et al. (1995) Ann. Rev. of Phar. & Toxicology 35, 257–276.
21. Goldman, M. J., et al. (1995) Nature Genetics 9, 126–131.
22. Engelhardt, J. F., et al. (1993) Nature Genetics 4, 27–34.
23. Zsengeller, Z. K., et al. (1995) Hum. Gene Ther. 6, 457–467.
24. Zabner, J., et al. (1994) Hum. Gene Ther. 5, 585–593.
25. Johnson, L. G., et al. (1992) Nature Genetics 2, 21–25.
26. Knowles, M. R., et al. (1995) N. Engl. J. Med. 333, 823–831.
27. Lozier, J. N., et al. (1994) JAMA 271, 47–51.
28. Kurachi, K., et al. (1993) Thrombosis & Homeostasis 70, 193–197.
29. Kozarsky, K., et al. (1993) Somat. Cell Mol. Genet. 19, 449–458.
30. Strauss, M. (1994) Gene Therapy 1, 156–164.
31. Ye, X., et al. (1996) J of Biol. Chem. 271, 3639–3646.
32. Douglas, J. T., et al. (1997) Science and Medicine XXXX 44–53.
33. Hehir, K. M., et al. (1996) J. Virol. 70, 8459–8467.
34. Kanegae, Y., et al. (1995) Nucleic Acids Res. 23, 3816–3821.

35. Hardy, S., et al. (1997) J. Virol. 71, 1842–1849.
36. Douglas, J. T., et al. (1995) Tumor Targeting 1, 67–84.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

wherein said Bcl-2 gene is expressed in said liver graft, wherein reduced number of apoptotic cell in said graft due to Bcl-2 gene expression leads to improved organ preservation of said liver graft.

3. A method of cytoprotecting endothelial cells during cold preservation, comprising the steps of:
transfecting said endothelial cells with an adenovirus vector encoding an anti-apoptotic Bcl-2 gene; before cold preservation and
wherein said Bcl-2 gene is expressed in said endothelial cells, wherein reduced number of apoptotic cell in said endothelial cells due to Bcl-2 gene expression leads to cytoprotection of said endothelial cells during cold preservation.

4. A method of cytoprotecting pancreatic islet cells, comprising the steps of:
transfecting said pancreatic islet cells with an adenovirus vector encoding an anti-apoptotic Bcl-2 gene; before cold preservation and

What is claimed is:

1. A method of reducing ischemia/reperfusion injury in the liver of an individual in need of such treatment, comprising the steps of:
administering systemically an adenoviral vector encoding an anti-apoptotic Bcl-2 gene under the control of a cytomegalovirus promoter to said individual; and
wherein said Bcl-2 genes is expressed in the liver of said individual, wherein reduced number of apoptotic cell in the liver due to Bcl-2 gene expression leads to reduced ischemia/reperfusion injury in the liver of said individual.

2. A method of improving organ preservation of liver graft, comprising the steps of:
administering systemically an adenoviral vector encoding an anti-apoptotic Bcl-2 gene before procurement of said liver graft; and wherein said Bcl-2 gene is expressed in said pancreatic islet cells, wherein reduced number of apoptotic cells in said pancreatic islet cells due to Bcl-2 gene expression leads to cytoprotection of said pancreatic islet cells.

5. A method of increasing expression of a transgene in the liver of an individual, comprising the steps of:
administrating by systemic administration an adenoviral vector encoding an anti-apoptotic Bcl-2 gene and an adenoviral vector encoding said transgene to said individual; and
wherein said Bcl-2 gene is co-expressed with said transgene in the liver cells of said individual, wherein decreased incidence of apoptosis in said liver cells due to Bcl-2 gene expression results in increased expression of said transgene in the liver of said individual.

6. The method of claim 5, wherein said method increases the expression of said transgene in said cell by up to 2 log.

* * * * *